(12) United States Patent
Stahl et al.

(10) Patent No.: US 7,750,149 B2
(45) Date of Patent: Jul. 6, 2010

(54) SEVEN-MEMBERED HETEROCYCLIC CARBENES AND THEIR METAL COMPLEXES

(75) Inventors: Shannon S. Stahl, Madison, WI (US); Christopher C. Scarborough, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 787 days.

(21) Appl. No.: 11/102,964

(22) Filed: Apr. 11, 2005

(65) Prior Publication Data

US 2006/0229448 A1 Oct. 12, 2006

(51) Int. Cl.
C07D 487/00 (2006.01)
(52) U.S. Cl. ...................................... 540/471
(58) Field of Classification Search ............... None
See application file for complete search history.

(56) References Cited

U.S. PATENT DOCUMENTS

| | | | |
|---|---|---|---|
| 6,552,139 | B1 | 4/2003 | Herrmann et al. |
| 6,635,768 | B1 | 10/2003 | Herrmann et al. |
| 6,787,620 | B2 | 9/2004 | Herrmann et al. |
| 6,838,489 | B2 | 1/2005 | Bell et al. |
| 2003/0149273 | A1 | 8/2003 | Militzer et al. |

FOREIGN PATENT DOCUMENTS

| | | |
|---|---|---|
| EP | 0 798 041 A | 10/1997 |
| WO | WO 98/27064 A1 | 6/1998 |
| WO | WO 01/66248 A2 | 9/2001 |

OTHER PUBLICATIONS

"Substructure search", http://www.sigmaaldrich.com/catalog/search/SubstructureSearchPage, accessed Oct. 2, 2008.*
STN search (Nov. 24, 2009).*
Alder et al., (1999), Complexation of stable carbenes with alkali metals, *J. Chem. Commun.*, 241-242.
Alder et al., (2001), Preparation of tetraalkylformamidinium salts and related species as precursors to stable carbenes, *J. Che. Soc., Perkin Trans*, 1., 1586-1593.
Arduengo et al., (1991), A Stable Crystalline Carbene, *J. Am. Chem Soc.*, 113:361-363.
Arduengo (1990), Looking for Stable Carbenes: The Difficulty in Starting Anew, *Acc. Chem. Res.*, 32:913-921.
Bazinet et al., (2003), Constructing a Stable Carbene with a Novel Topology and Electronic Framework, *J. Am. Chem. Soc.*, 125:13314-13315.
Bourissou et al., (2000), Stable Carbenes, *Chem. Rev.*, 100:39-92.
Despagnet-Ayoub & Grubbs, (2004), A Stable Four-Membered N-Heterocyclic Carbene, *J. Am. Chem. Soc.*, 126:10198-10199.
Despagnet-Ayoub & Grubbs, (2005), A Ruthenium Olefin Metathesis Catalyst with a Four-Membered N-Heterocyclic Carbene Ligand, *Organometallics*, 24:338-340.
Enders et al., (1996), A Novel Asymmetric Benzoin Reaction Catalyzed by a Chiral Triazolium Salt, *Helv. Chim. Acta.*, 79:1217-1221.

Enders & Balensiefer, (2004), Nucleophilic Carbenes ini Asymetric Organocatalysis, *Acc. Chem. Res.*, 37:534-541.
Gillespie et al., (2002), Enantioselective Aziridination Using Copper Complexes of Biaryl Schiff Bases, *J. Org, Chem.*, 67:3450-3458.
Guillen et al., (2001), Enantioiselective Copper-catalyzed conjugate addition using chiral diaminocarbene ligands, *Tetrahedron: Asymmetry*, 12:2083-2086.
Hall & Rzepa, (2003), Möbius bis and tris-spiroaromatic systems, *Org. Biomol. Chem.*, 1:182-185.
Herrmann & Köcher, (1997), Essays on organometallic chemistry: 9. N-heterocyclic carbenes, *Tetrahedron Lett.*, 36:2162-2187.
Herrmann et al., (2001), Metal Complexes of Stable Carbenes, *Angew. Chem, Int. Ed. Engl., Adv. Organomet. Chem.*, 48:1-69.
Herrmann (2002), N-heterocyclic carbenes. Part 31. N-heterocyclic carbenes: A new concept in organometallic catalysts, *Angew. Chem. Int. Ed.*, 41:1290-1309.
Jensen & Sigman, (2003), Palladium Catalysts for Aerobic Oxidative Kinetic Resolution of SEcondary Alcohols Based on Mechanistic Insight, *Org. Lett.*, 5:63-65.
Kastrup, Oldfield, & Rzepa, (2002), An *ab initio* computational study of monodentate palladium ligand complexes with Möbius-aromatic chiral character, *J. Chem. Soc., Dalton Trans.*, 2421-2422.
Lee & Hu, (2004), Density Functional Study of *N*-Heterocyclic and Diamino Carbene Complexes: Comparison with Phosphines, *Organometallics*, 23:976-983.
Perry & Burgess (2003), Chiral *N*-heterocyclic carbene-transition metal complexes in asymmetric catalysis, Tetrahedron: *Asymmetry*, 14:951-961.
Perry et al., (2003), Optically Active Iridium Imidazol-2-ylidene-oxazoline Complexes: Preparation and Use of Asymmetric Hydrogenation of Arylalkenes, *J. Am. Chem. Soc.*, 125:114-123.
Reetz et al., (2003), Binaphthyldiamine-Based Diazaphospholidines as a New Class of Chiral Monodentate P-Ligands, *Synthesis*, 12:1809-1814.
Saba et al., (1991), One-Pot Synthesis of Cyclic Amidinium Tetrafluoroborates and Hexafluorophosphates; The Simplest Models of $N^5,N^{10}$-Methenyltetrahydrofolaate Coenzyme. *Tetrahedron Lett.*, 32:5031-4.

(Continued)

*Primary Examiner*—James O Wilson
*Assistant Examiner*—Noble Jarrell
(74) *Attorney, Agent, or Firm*—Joseph T. Leone, Esq.; DeWitt Ross & Stevens S.C.

(57) ABSTRACT

Disclosed are carbenes of the general formula:

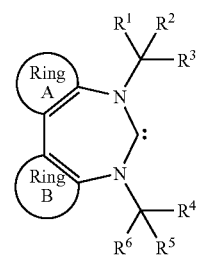

and including salts thereof, and metal complexes thereof. The carbenes are useful in any reaction where carbenes and carbene-metal complexes are used. The carbenes disclosed herein are particularly useful in asymmetric catalysis.

5 Claims, 10 Drawing Sheets

OTHER PUBLICATIONS

Seiders et al., (2001), Enantioselective Ruthenium-Catalyzed Ring-Closing Metathesis, *Org. Lett.,* 3:3225-3228.

Stauffer et al., (2000), High Turnover Number and Rapid, Room-Temperature Amination of Chloroarenes Using Saturated Carbene Ligands, *Org. Lett.,* 2:1423.

Tang & Zhang, (2004), New Chiral Phosphorus Ligands for Enantioselective Hydrogenation, *Chem. Rev.,* 103:3029-3069.

Trnka & Grubbs, (2001), The Development of $L_2X_2Ru=CHR$ Olefin Metathesis Catalysts: An Organometallic Success Story, *Acc. Chem. Res.,* 34:18-29.

Teles et al., (1996), The Chemistry of Stable Carbenes, Part 2. Benzoin-type Condensations of Formaldehyde Catalyzed by Stable Carbenes, *Helv. Chim. Acta,* 79:61-83.

Van Veldhuizen, (2002), A Recyclable Chiral Ru Catalyst for Enantioselective Olefin Metathesis. Efficient Catalytic Asymmetric Ring-Opening/Cross Metathesis in Air, *J. Am. Chem. Soc.,* 124:4954-4955.

Viciu et al., (2004), Synthetic and Ctructural Studies of (NHC)Pd(allyl)Cl Complexes (NHC = *N*-heterocyclic carbene), *Organometallics,* 23:1629-1635.

Yang et al., (2001), Highly Efficient Heck Reactions of Aryl Bromides with *n*-Butyl Acrylate Mediated by a Palladium/Phosphine-Imidazolium Salt System, *Org. Lett.,* 3:1511.

Zimmerman, (1971), The Möbius-Hückel Concept in Organic Chemistry. Application to Organic Molecules and Reactions, *Acc. Chem. Res.,* 4:272-280.

Heilbronner (1964), Hückel Molecular Orbitals of Möbius-type conformations, 29:1923-1928.

Scarborough, C., et al. "$Pd^{II}$ Complexes Possessing a Seven-Membered N-Heterocyclic Carbene Ligand," *Andew. Chem.,* 2005, vol. 117, pp. 5403-5406, XP002390758.

Kastrup, C., et al. "The aromaticity and Möbius characteristics of carbeno[8]heteroannulenes and triplet state annulenes," *Chem. Commun.,* 2002, pp. 642-643, XP002390762.

\* cited by examiner

SEVEN-MEMBERED HETEROCYCLIC CARBENES AND THEIR METAL COMPLEXES

FEDERAL FUNDING STATEMENT

This invention was made with United States government support awarded by the following agency: NIH GMO67173. The United States has certain rights in this invention.

BACKGROUND

Since the discovery of stable N-heterocyclic carbenes (NHCs), these complexes have found widespread use in catalysis, serving both as nucleophilic catalysts and as ligands in metal-mediated reactions. See, for example, Arduengo et al. (1991) *J. Am. Chem. Soc.* 113:361-363; Arduengo (1999) *Acc. Chem. Res.* 32:913-921; Bourissou et al. (2000) *Chem. Rev.* 100:39-92; and Herrmann & Köcher (1997) *Angew. Chem., Int. Ed. Engl.* 36:2162-2187. See also Enders & Balensiefer (2004) Acc. Chem. Res. 37:534-541; Herrmann et al. (2001) *Adv. Organomet. Chem.* 48:1-69; Herrmann (2002) *Angew. Chem. Int. Ed.* 41:1290-1309; and Perry & Burgess (2003) *Tetrahedron: Asymmetry* 14:951-961.

A variety of heterocyclic frameworks have been employed in the preparation of NHCs, including four-, five- and six-membered rings, as represented by compounds 1 through 5). To date, most catalytic applications employ the five-membered analogs.

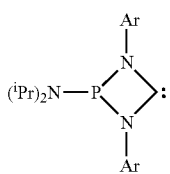

1

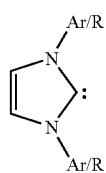

2

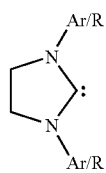

3

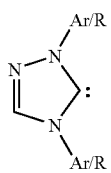

4

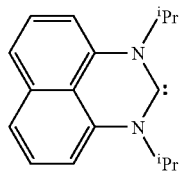

5

See, for example, the references cited above. For exceptions with 4- and 6-membered NHCs, see Despagnet-Ayoub & Grubbs (2004) *J. Am. Chem. Soc.* 126:10198-10199; Despagnet-Ayoub & Grubbs (2005) *Organometallics* 24:338-340; Alder et al. (1999) *J. Chem. Commun.* 241-242; Guillen et al. (2001) *Tetrahedron: Asymmetry* 12:2083-2086; and Bazinet et al. (2003) *J. Am. Chem. Soc.* 125:13314-13315.

NHC ligands are electronically similar to phosphines (see Herrmann & Köcher (1997) *Angew. Chem., Int. Ed. Engl.* 36:2162-2187; Lee & Hu (2004) *Organometallics* 23:976-983). Based on the widespread success of chiral phosphines in asymmetric catalysis (see Tang & Zhang (2004) *Chem. Rev.* 103:3029-3069), chiral NHCs have significant utility.

However, conventional heterocyclic carbenes suffer from one shared limitation: the nearly planar heterocyclic framework of these ligands constrains the spatial display of substituents bonded to the heterocyclic ring. As a consequence of the planarity (or near planarity) of these compounds, their successful application to asymmetric catalysis (i.e., ≧90% enantiomeric excess) remains limited. See, for example, Perry & Burgess (2003) *Tetrahedron: Asymmetry* 14:951-961.

In the patent literature, the synthesis and various applications of NHCs have been described. For examples that describe the synthesis and use of 5-membered NHCs, see Khasnis et al., WO9827064 and Millitzer et al., U.S. Patent Application Publication 2003/0149273. For examples that describe various NHC-containing olefin-metathesis catalysts, see Bell et al., U.S. Pat. No. 6,838,489, which describes catalysts generated using a thermally activated NHC precursor. See also Herrmann et al., U.S. Pat. No. 6,635,768, which describes alkylidene complexes of ruthenium-containing NHC ligands and their use as selective catalysts for olefin metathesis. Along the same lines, see, Herrmann et al., U.S. Pat. No. 6,787,620, and Herrmann et al., U.S. Pat. No. 6,552,139. For examples of NHC-metal complexes and their use in coupling reactions, see Lee et al., WO0166248.

There remains, however, a clear and unmet need for chiral NHCs that can be used as catalysts or ligands in asymmetric synthesis. The ability to synthesize, isolate, and prepare metal complexes of NHCs that possess a non-planar heterocyclic framework has significant utility toward this end.

SUMMARY OF THE INVENTION

The present invention is directed to 7-membered, N-heterocyclic carbenes, salts thereof, and metal complexes thereof. The carbenes are generally of formula I, metal complexes of formula I, and salts of formula I:

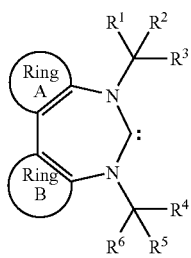

FORMULA I

Ring A and ring B are independently selected from the group consisting of substituted or unsubstituted mono- or polycyclic cycloalkenyl, cycloaryl, heterocycloaryl, and heterocycloalkenyl having up to 34 atoms within each of ring A or ring B; wherein heteroatoms in either of ring A or ring B, if any, are independently selected from the group consisting of N, O, S, and P.

$R^1$, $R^2$, $R^3$, $R^4$, $R^5$, and $R^6$ are independently selected from the group consisting of hydrogen; $C_1$ to $C_{60}$ substituted or unsubstituted, linear or branched alkyl, alkenyl, and alkynyl, aryl and heteroaryl; or $R^1$, $R^2$, and $R^3$, including or excluding the carbon to which they are attached and independent of $R^4$, $R^5$, and $R^6$, and $R^4$, $R^5$, and $R^6$, including or excluding the carbon to which they are attached and independent of $R^1$, $R^2$, and $R^3$, define a $C_3$ to $C_{60}$, substituted or unsubstituted, mono- or polycyclic cycloalkyl, cycloalkenyl, cycloalkynyl, cycloaryl, heterocycloaryl, heterocycloalkenyl, heterocycloaklynyl, wherein heteroatoms in, if any, are independently selected from the group consisting of N, O, S, and P.

Where substituents are present on any of rings A and B or any of the R moieties, the substituents are selected from the group consisting of halogen; linear or branched $C_1$-$C_{12}$-alkyl, alkenyl, or alkynyl; $C_5$-$C_{12}$-cycloalkyl, cylcoalkenyl, or cylcoalkynyl; mono- or polycyclic aryl, and mono- or polycyclic heteroaryl having up to 5 heteroatoms selected from N, O, S, and P.

The present invention explicitly encompasses the free carbenes (as illustrated in formula I), metal complexes of formula I, and salts of formula I.

In the preferred embodiment, ring A and ring B are selected from the group consisting of phenyl, naphthyl, anthracenyl, phenanthracenyl, and pyrenyl, pyridinyl, pyrrolidinyl, quinoline, indole, and thiophene. Also in the preferred embodiment, $R^1$, $R^2$, $R^3$, $R^4$, $R^5$, and $R^6$ are independently selected from the group consisting of hydrogen; $C_1$ to $C_{60}$ substituted or unsubstituted, linear or branched alkyl, alkenyl, and alkynyl, aryl and heteroaryl.

The present invention also encompasses carbenes formula II, metal complexes of formula II, and salts of formula II:

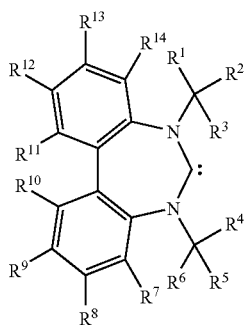

FORMULA II

Here, $R^1$ through $R^6$ are as defined previously.

$R^7$, $R^8$, $R^9$, $R^{10}$, $R^{11}$, $R^{12}$, $R^{13}$, and $R^{14}$ are independently selected from the group consisting of hydrogen, halide, $C_1$ to $C_{60}$ substituted or unsubstituted, linear or branched alkyl, alkenyl, and alkynyl, aryl, heteroaryl, cyano, thiolate, alkoxy, primary amido, and secondary amido; or any of $R^7$, $R^8$, $R^9$, and $R^{10}$ combined and any of $R^{11}$, $R^{12}$, $R^{13}$, and $R^{14}$ combined independently define substituted or unsubstituted mono- or polycyclic cycloalkenyl, cycloaryl, heterocycloaryl, and heterocycloalkenyl fused rings having up to 34 atoms; wherein heteroatoms, if present, are independently selected from the group consisting of N, O, S, and P.

More specifically still, the carbenes of the present invention comprise formula III complexes:

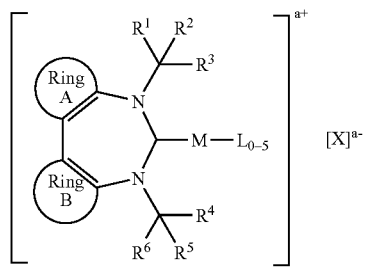

FORMULA III

Here, ring A, ring B, $R^1$, $R^2$, $R^3$, $R^4$, $R^5$, and $R^6$ are as defined as defined previously. M is hydrogen or a metal. L (when present) is one or more ligand(s) coordinated to M. When there is more than one ligand (L), each L substituent may be the same or different [e.g., $L_3$ explicitly encompasses (L')(L")(L''')]. X is any counter-anion (or group of counter-anions) without limitation, and "a" is an integer.

In the preferred formula III carbenes, M is hydrogen or a metal selected from the group consisting of Fe, Co, Ni, Cu, Ru, Rh, Pd, Ag, Os, Ir, Pt, and Au, and X is selected from the group consisting of tetrafluorborate, hexafluorophosphate, and halide.

In formulae I and III, the most preferred compounds are those wherein rings A and B are phenyl or naphthyl. Likewise, in formula II, the most preferred compounds are those wherein $R^7$, $R^8$, $R^9$, $R^{10}$, $R^{11}$, $R^{12}$, $R^{13}$, and $R^{14}$ are hydrogen, or wherein any of $R^7$, $R^8$, $R^9$, and $R^{10}$ combined, and any of $R^{11}$, $R^{12}$, $R^{13}$, and $R^{14}$ combined define a fused phenyl ring.

DETAILED DESCRIPTION OF THE INVENTION

Definitions

The following definitions are provided for sake of clarity. Terms got explicitly defined are to be given their accepted definitions in the field of organic chemistry in general, and the field of synthetic organic chemistry in particular.

Where compounds are designated by chemical structure drawings, without any designation of stereoisomerism or positional isomerism (e.g., cis vs. trans isomerism), the structure explicitly encompasses all such stereoisomers, positional isomers, enantiomers, diastereomers, enantiomerically pure or enantiomerically enriched forms thereof, and racemic mixtures thereof.

The term "metal" refers to any metal on the periodic chart of the elements. Transition and main group metals of Group 3 to Group 13 are preferred, and metals of Groups 8-11 (Fe, Co, Ni, Cu, Ru, Rh, Pd, Ag, Os, Ir, Pt and Au) are most preferred.

Regarding salts of the subject compounds, the subject compounds disclosed herein are carbenes. As such, the carbene carbon is a neutral species, having two single bonds to neighboring atoms (nitrogen atoms in this instance) and a pair of non-bonding electrons. In its neutral state, however, the carbene carbon has only six electrons, and is stabilized by donation of adjacent nitrogen lone pair electron density to the empty carbon orbital to alleviate the electron deficiency. Coordination of a proton to the nonbonding pair of electrons of the carbene results in the formation of an amidinium salt that may possess any of numerous possible counter-anions, e.g. halides, tetrafluoroborate, hexafluorophosphate, etc.

Chemistry:

Exemplary of the subject compounds is the axially chiral, seven-membered N-heterocyclic carbene (NHC), compound 8:

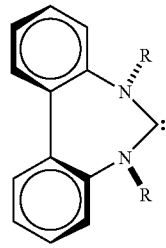

Compound 8 where R is adamantyl.

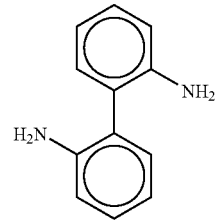

Compound 9$^H$

The initial synthetic efforts targeted analogs of 8 with bulky aryl substituents (e.g., R=mesityl; 2,6-diisopropylphenyl), which are commonly found in stable NHCs. Compound 9$^H$ was obtained in quantitative yield by reduction of 2,2'-dinitrobiphenyl, and mesitylation of 9$^H$ proceeds effectively under previously reported conditions. See Reetz et al. (2003) *Synthesis* 12:1809-1814. The subsequent condensation step to form the amidinium salt, however, was unsuccessful using a variety of known protocols:

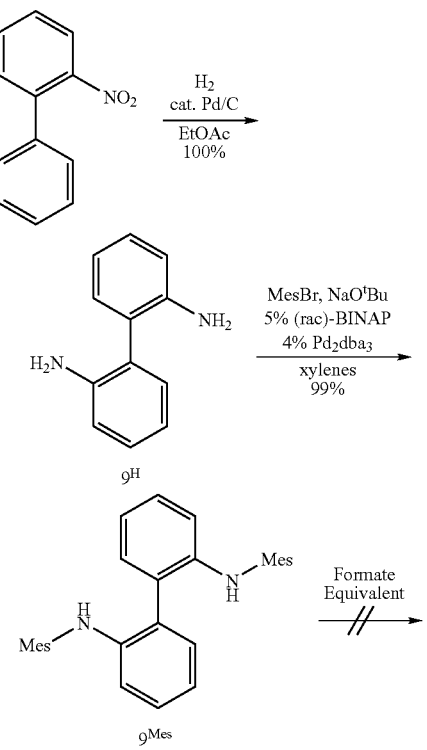

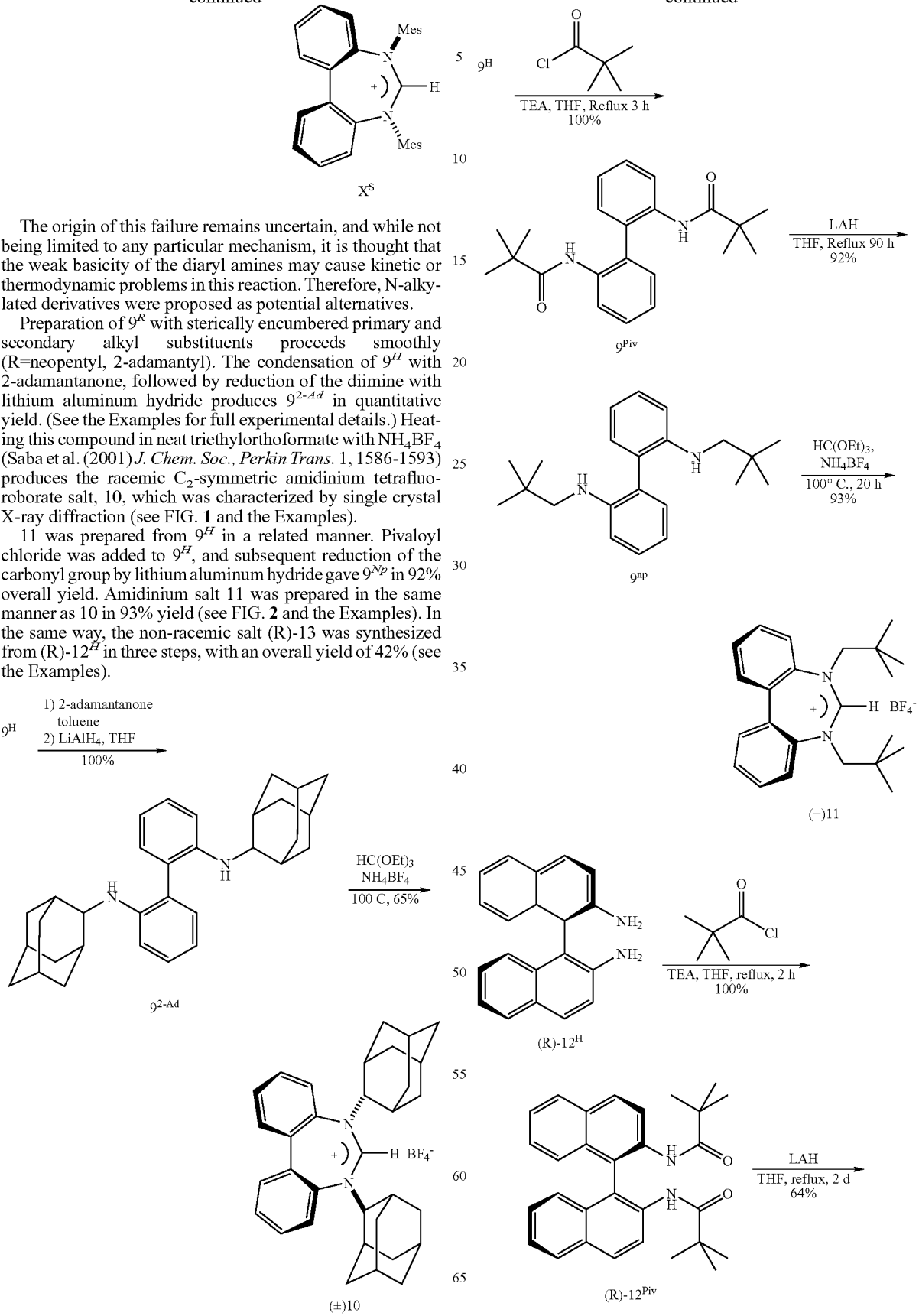

The origin of this failure remains uncertain, and while not being limited to any particular mechanism, it is thought that the weak basicity of the diaryl amines may cause kinetic or thermodynamic problems in this reaction. Therefore, N-alkylated derivatives were proposed as potential alternatives.

Figure 1:
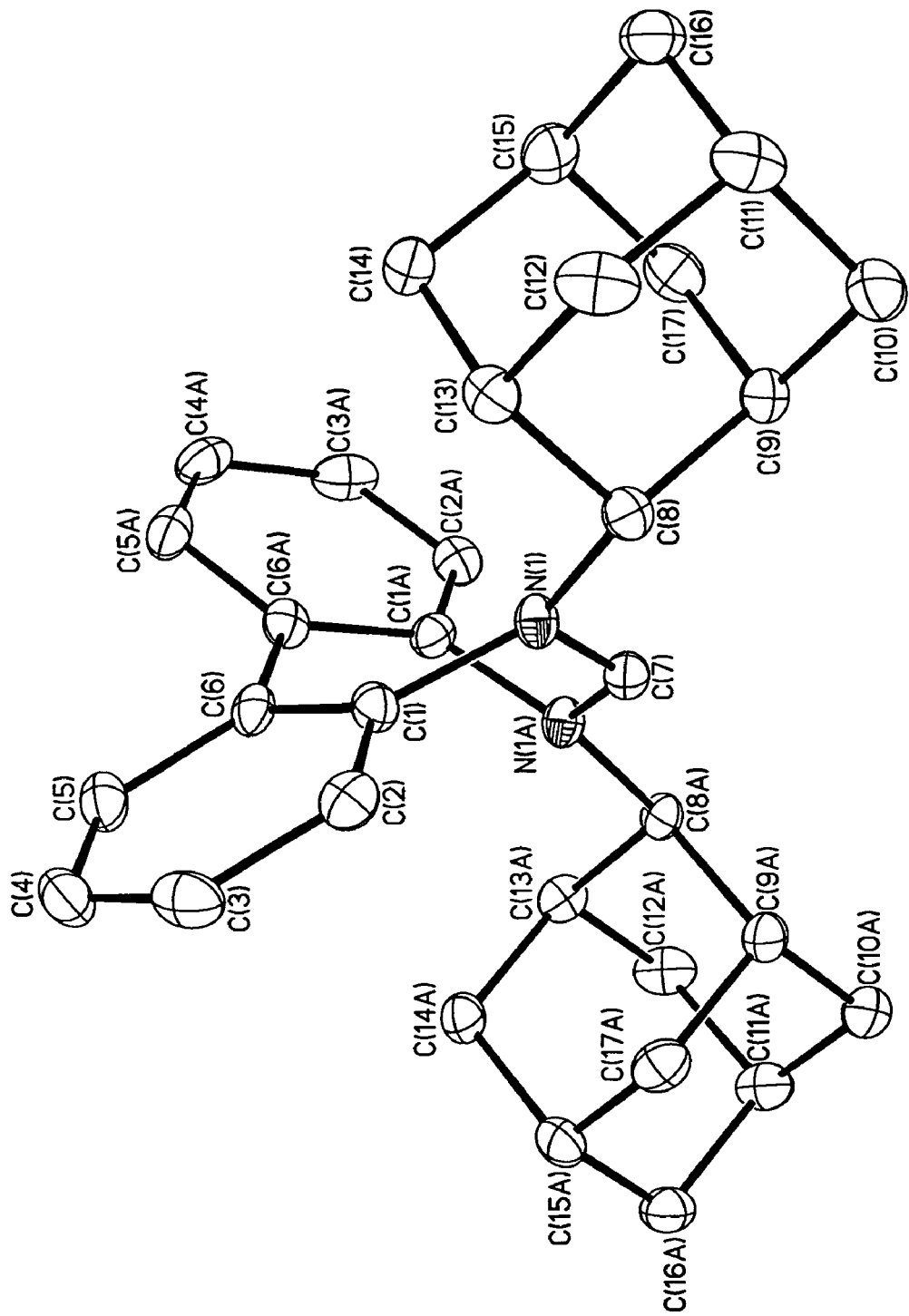
FIG. 1 is a depiction of the molecular structure of compound 10 as revealed by single-crystal X-ray diffraction. The hydrogen atoms and the BF4-counterion are omitted for clarity. Thermal ellipsoids are shown at 50% probability.

Preparation of $9^R$ with sterically encumbered primary and secondary alkyl substituents proceeds smoothly (R=neopentyl, 2-adamantyl). The condensation of $9^H$ with 2-adamantanone, followed by reduction of the diimine with lithium aluminum hydride produces $9^{2-Ad}$ in quantitative yield. (See the Examples for full experimental details.) Heating this compound in neat triethylorthoformate with $NH_4BF_4$ (Saba et al. (2001) *J. Chem. Soc., Perkin Trans.* 1, 1586-1593) produces the racemic $C_2$-symmetric amidinium tetrafluoroborate salt, 10, which was characterized by single crystal X-ray diffraction (see FIG. 1 and the Examples).

11 was prepared from $9^H$ in a related manner. Pivaloyl chloride was added to $9^H$, and subsequent reduction of the carbonyl group by lithium aluminum hydride gave $9^{Np}$ in 92% overall yield. Amidinium salt 11 was prepared in the same manner as 10 in 93% yield (see FIG. 2 and the Examples). In the same way, the non-racemic salt (R)-13 was synthesized from (R)-$12^H$ in three steps, with an overall yield of 42% (see the Examples).

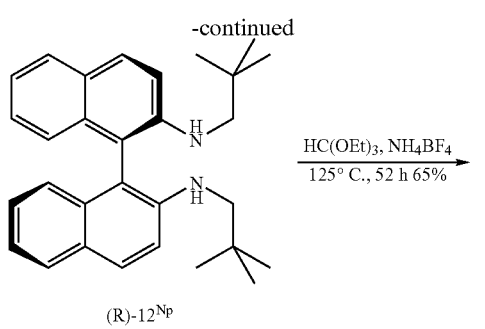

(R)-12^Np

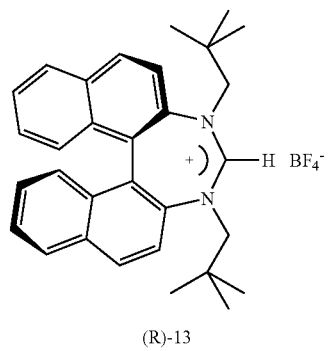

(R)-13

The amidinium salts 10, 11, and (R)-13 represent attractive NHC precursors. Efforts were then focused on preparing NHC-coordinated palladium(II) complexes. Deprotonation of 10 in a THF solution of [Pd(allyl)Cl]$_2$ (Jensen & Sigman (2003) *Org. Lett.* 5:63-65, Viciu et al. (2004) *Organometallics* 23:1629-1635) generates the air-stable NHC—Pd(allyl)Cl complex, 14, in high yield. The $^1$H NMR spectrum of 14 reveals the presence of two diastereomeric allyl rotamers in solution in a 1.4:1 ratio. Single-crystal X-ray diffraction studies confirmed the structure of 14 (see FIG. 3) and revealed that a mixture of isomers is also present in the solid state, with the allyl group disordered over two positions in a 2.7:1 ratio. See FIG. 4 and the Examples.

Figure 6:
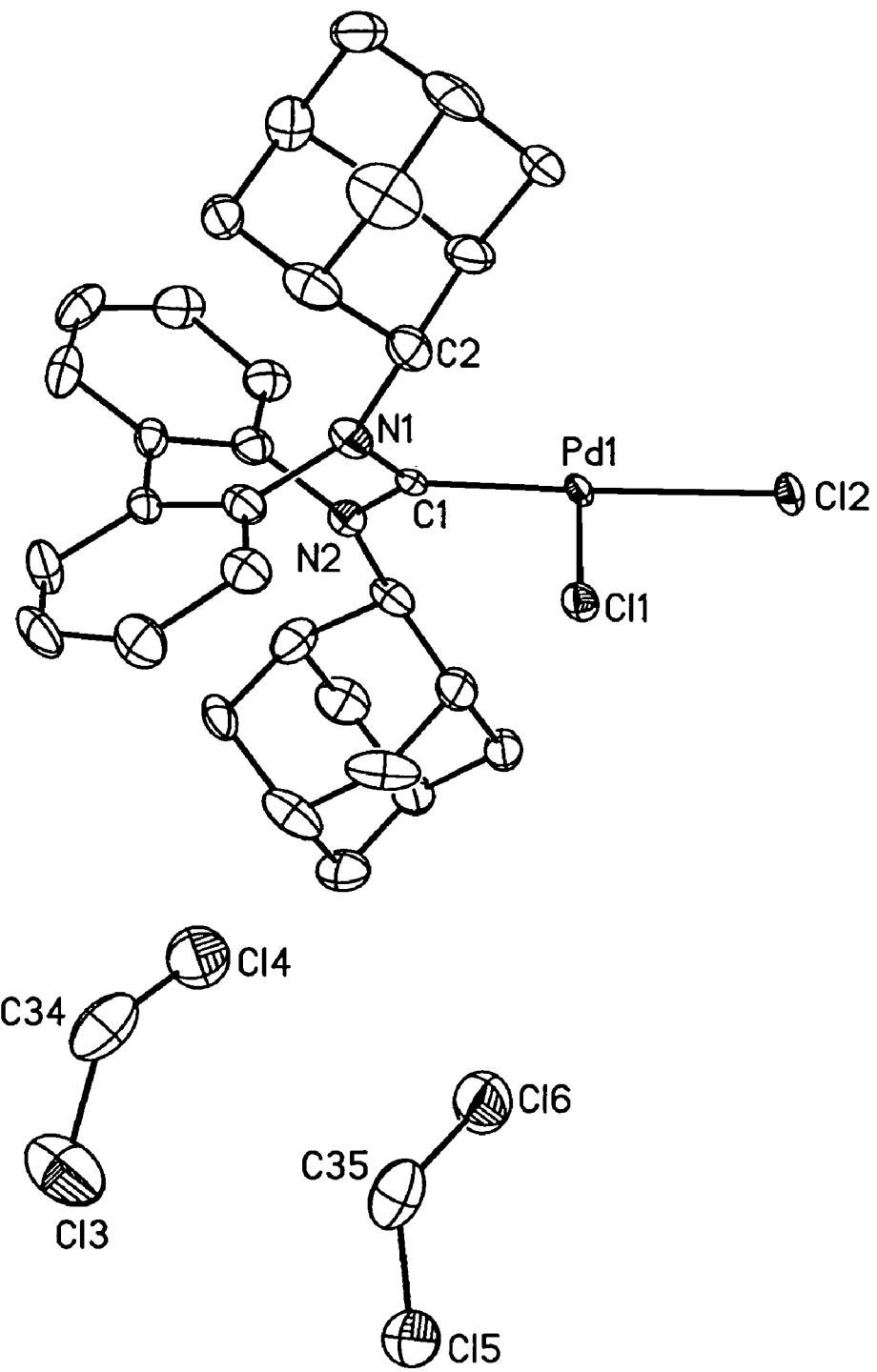
FIG. 6 is a depiction of the molecular structure of the asymmetric unit of the palladium complex 15 as revealed by single-crystal X-ray diffraction. The hydrogen atoms are omitted for clarity. Thermal ellipsoids are shown at 30% probability.
Figure 7:
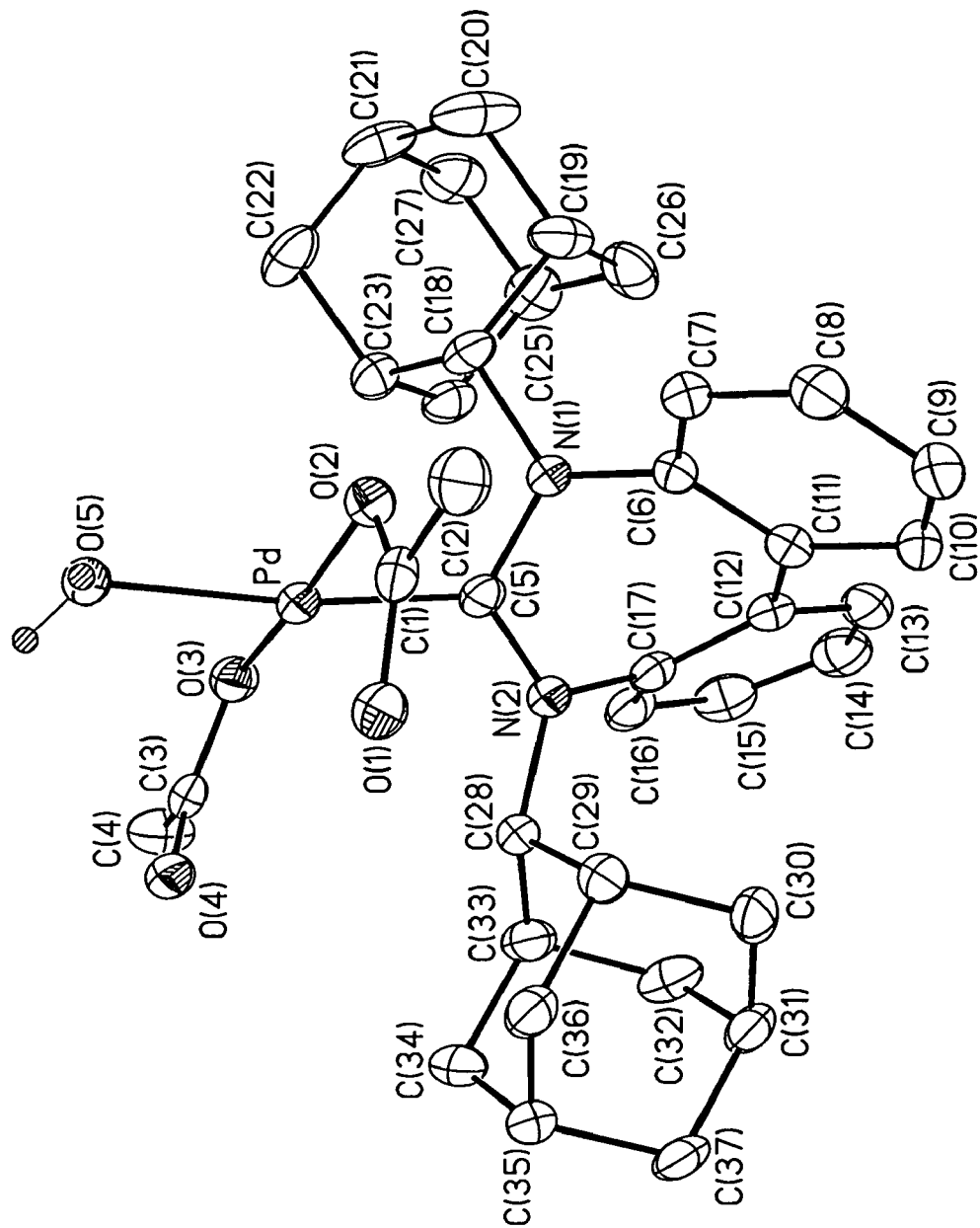
FIG. 7 is a depiction of the molecular structure of complex 16 as revealed by single-crystal X-ray diffraction. The hydrogen atoms except for those on the water ligand are omitted for clarity. Thermal ellipsoids are shown at 50% probability.
Figure 8:
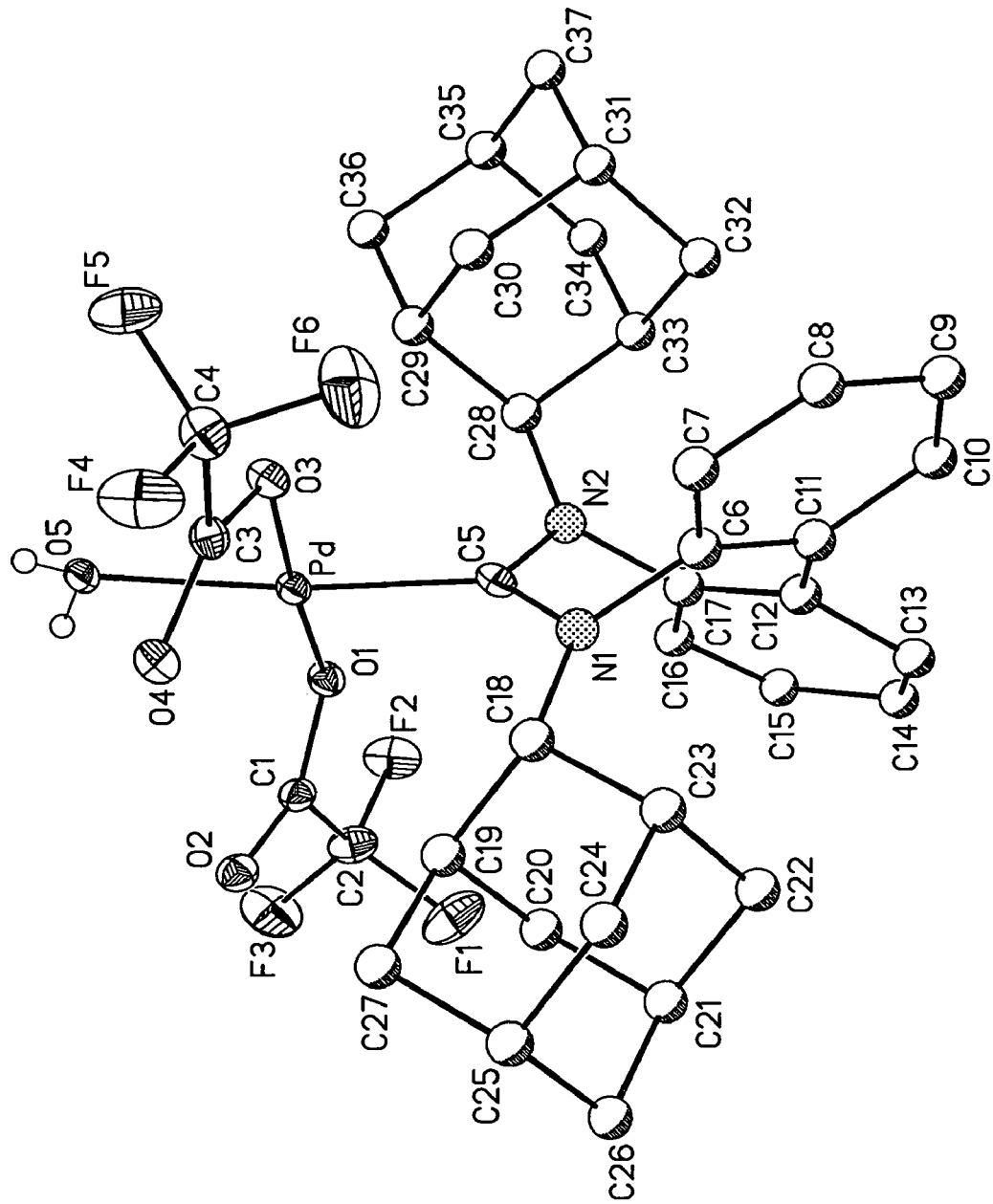
FIG. 8 is a depiction of the molecular structure of complex 17 as revealed by single-crystal X-ray diffraction. The hydrogen atoms except for those on the water ligand are omitted for clarity. Thermal ellipsoids are shown at 50% probability. Only the preferred orientation is shown.
Figure 9:
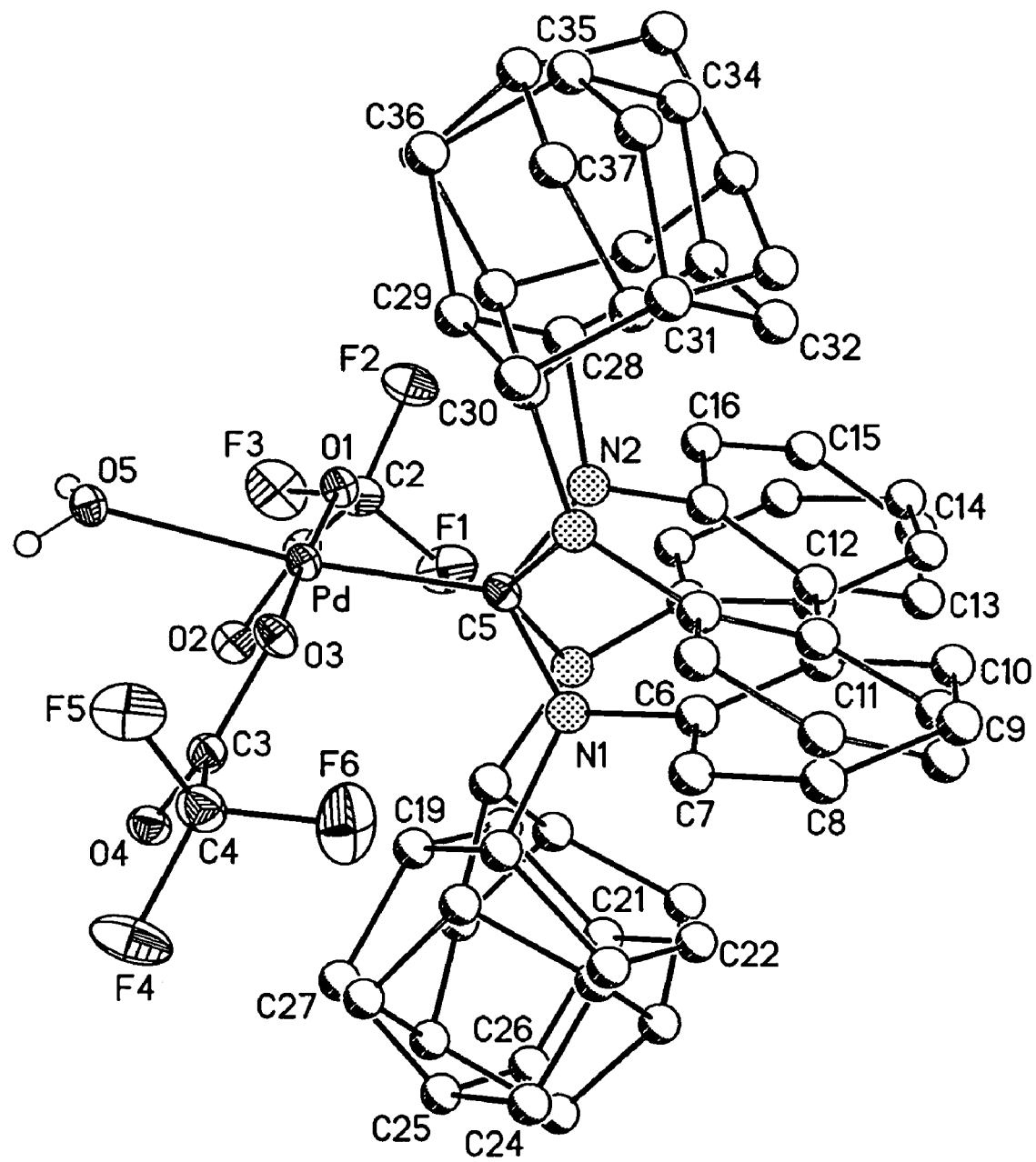
FIG. 9 is another depiction of molecular structure of the (NHC)—Pd(O$_2$CCF$_3$)$_2$(OH$_2$) complex 17 as revealed by single-crystal X-ray diffraction. The hydrogen atoms except for those on the water ligand are omitted for clarity. Thermal ellipsoids are shown at 50% probability. The NHC ligand is disordered.

Protonolysis of the allyl ligand of 14 with HCl in diethyl ether produces [NHC—Pd(Cl)$_2$]$_2$, 15, in quantitative yield. Only one isomer of this dimeric compound is detected in solution by $^1$H NMR spectroscopy. Single crystal X-ray diffraction studies reveal the presence of a heterochiral dimer (see FIGS. 5 and 6 and the Examples). Treatment of 15 with silver acetate or silver trifluoroacetate in wet CH$_2$Cl$_2$ yields the NHC—Pd carboxylate complexes 16 and 17, respectively (see FIGS. 7, 8 and 9)

Synthesis of NHC-Coordinated Pd(II) Complexes

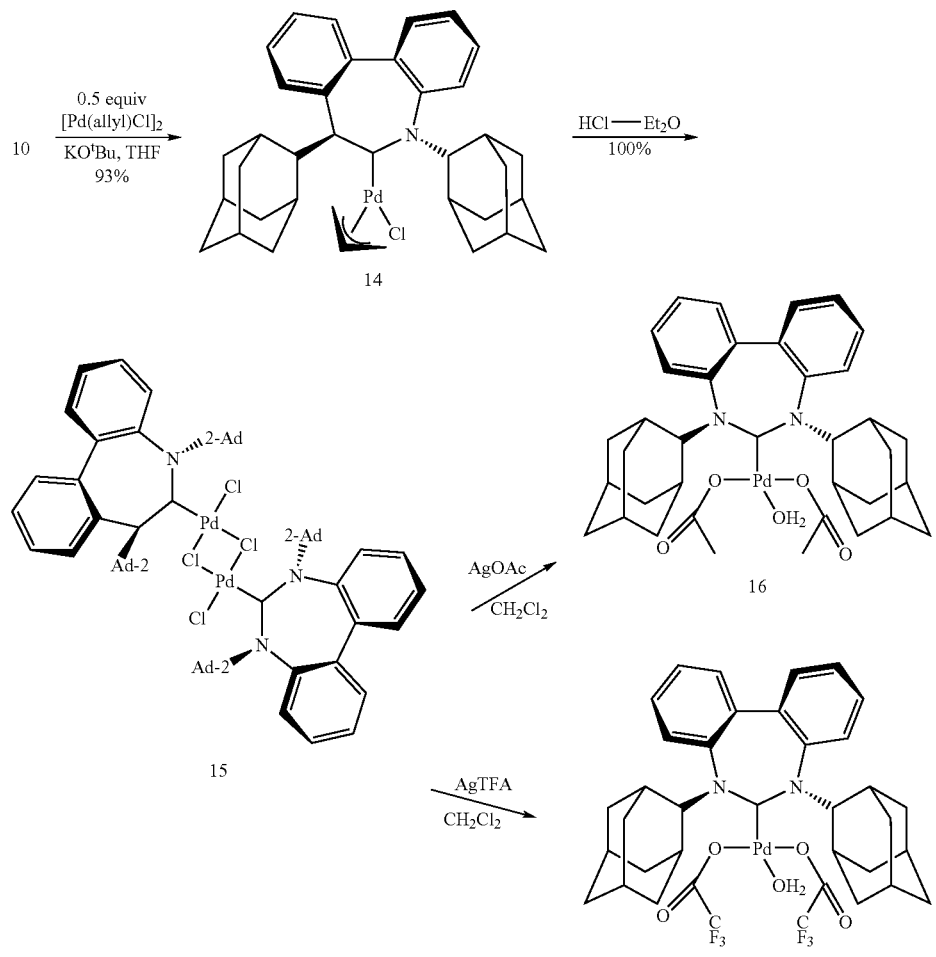

Figure 10:
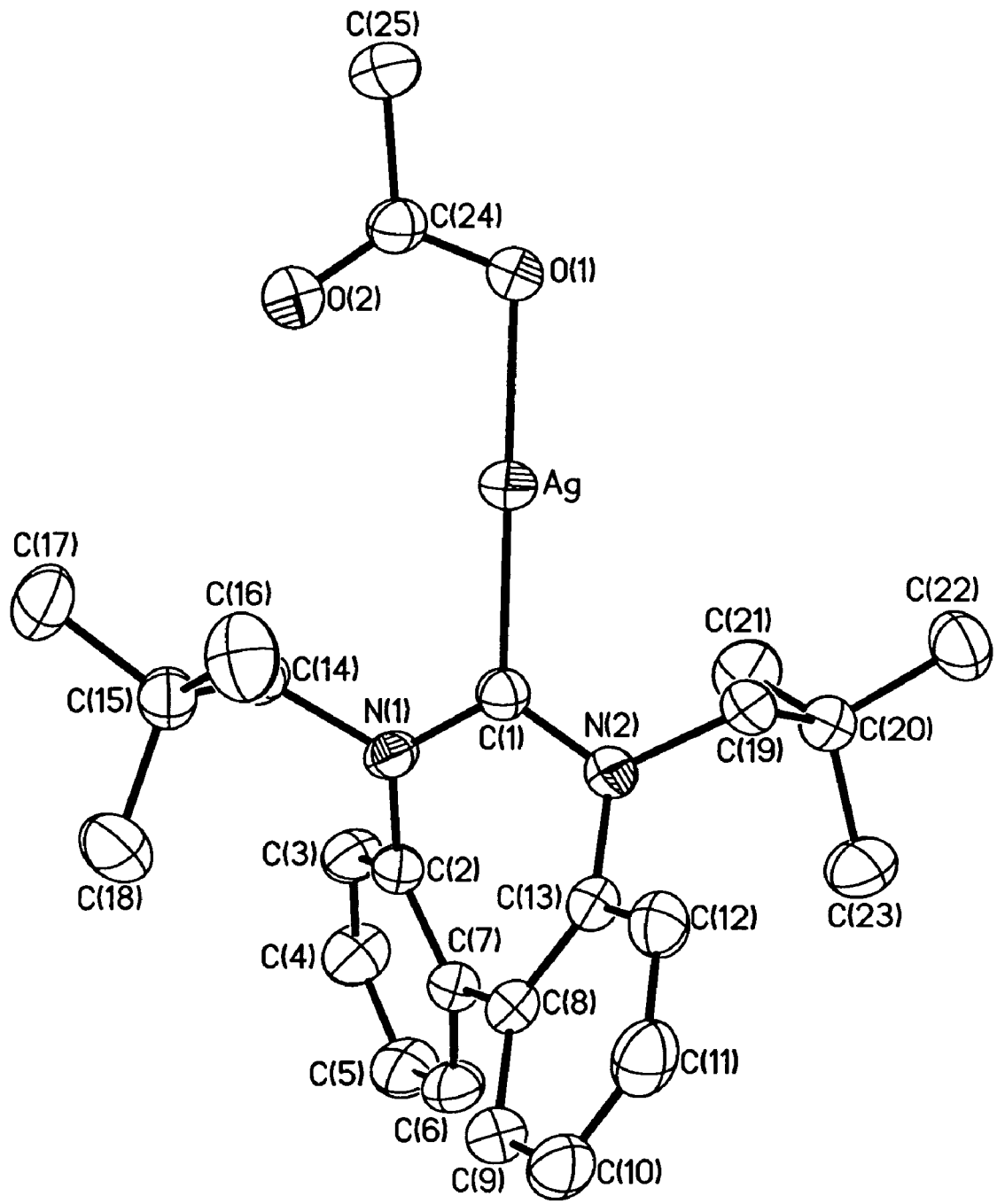
FIG. 10 is a depiction of the molecular structure of the (NHC)—Ag—OAc complex 18 as revealed by single-crystal X-ray diffraction. The hydrogen atoms are omitted for clarity. Thermal ellipsoids are shown at 50% probability.

Reaction of 11 with potassium tert-butoxide in the presence of Pd(OAc)$_2$ and NaI, followed by addition of AgOAc resulted in the formation of NHC—Ag—OAc complex 18 in 18% yield (See FIG. 10 and the Examples).

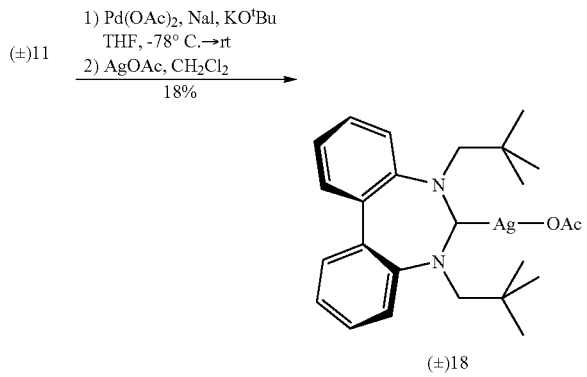

Rzepa and coworkers previously reported a purely computational analysis of 7-membered, 8-π-electron NHCs. See Kastrup, Oldfield, & Rzepa, (2002) J. Chem. Soc., Dalton Trans. 2421-2422. These ab initio computational studies revealed that significant reduction of the expected antiaromatic character arises from twisting of the strained heterocyclic ring allowing for Möbius-type aromatic stabilization. See Hall & Rzepa (2003) Org. Biomol. Chem. 1:182-185; Heilbronner (1964) Tetrahedron Lett. 29:1923-1928; and Zimmerman (1971) Acc. Chem. Res. 4:272-280. Rzepa's investigation, however, was purely computational, and Rzepa's group made no attempt to synthesize the compounds described therein.

The compounds disclosed herein are the first metal complexes of a seven-membered NHC. They posses a large torsional twist resulting in axial chirality and are synthesized via a route amenable to the preparation of diverse analogs. The C$_2$-symmetric architecture can be readily modified with different nitrogen substituents, and the biaryl backbone can be altered to include rotationally hindered and enantiomerically pure derivatives, for example, binaphthyl.

Utility:

The carbenes described herein are useful in any protocol or reaction scheme for synthesizing chemical compounds wherein other NHCs are conventionally used, without limitation. In particular, NHCs find use as nucleophilic catalysts and as ligands coordinated to metals in homogeneous metal-catalyzed transformations.

For examples of NHCs used as nucleophilic catalysts, see Teles et al. (1996) Helv. Chim. Acta 79:61-83, in which NHCs are used to catalyze the condensation of two aldehydes to form β-hydroxyketones. The above reaction type has been carried out—employing chiral NHCs to give optically active β-hydroxyketones in good yields and enantioselectivities (See Enders et al. (1996) Helv. Chim. Acta 79:1217-1221).

Examples of transition metal-NHC complexes as catalysts for organic transformations include, but are not limited to, amination of aryl halides catalyzed by NHC—Pd complexes (See Stauffer et al. (2000) Org. Lett. 2:1423), Heck coupling of arylboronic acids and aryl halides catalyzed by Pd—NHC complexes (Yang et al. (2001) Org. Lett. 3:1511), asymmetric ring-closing/opening olefin metathesis catalyzed by ruthenium complexes of chiral NHCs (see Van Veldhuizen et al. (2002) J. Am. Chem. Soc. 124:4954-4955 and Seiders, Ward and Grubbs (2001) Org. Lett. 3:3225-3228), and asymmetric hydrogenation of alkenes catalyzed by iridium complexes of chiral NHCs (See Perry et al. (2003) J. Am. Chem. Soc. 125:114-123).

The carbenes disclosed herein can be used in any of the above-noted types of reactions.

The most preferred use for the present compounds, however, is as enantioselective catalysts. Metal complexes according to the present invention are highly useful as catalysts for alkene metathesis reactions. For analogous reactions with other types of carbenes, see Trnka & Grubbs (2001) Acc. Chem. Res. 34:18-29. Thus, for example, metal complexes of the present compounds can be used to catalyze the asymmetric hydrogenation of alkenes, the hydrosilylation of methyl ketones, and the hydrosilylation of acetophenone. Complexes according to the present invention can also be used to catalyze enantioselective ring-opening and ring-closing metathesis reactions. See, for example, Seiders et al. (2001) Org. Lett. 3:3225-3228, and Van Veldhuizen et al. (2002) J. Am. Chem. Soc. 124:4954-4955.

EXAMPLES

The following Examples are included solely to provide a more complete description of the invention disclosed and claimed herein. The Examples do not limit the scope of the claimed invention in any fashion.

General: All manipulations were performed under an inert nitrogen atmosphere unless otherwise specified. Dry, oxygen-free solvents were employed. $^1$H and $^{13}$C NMR spectra were recorded on either a Bruker Homer-300, a Bruker Athena-300, a Varian Mercury-300 or a Varian Inova-500 NMR spectrometer. $^1$H chemical shifts are reported in ppm relative to Me$_4$Si as an external standard, while $^{13}$C chemical shifts are reported in ppm relative to CHCl$_3$.

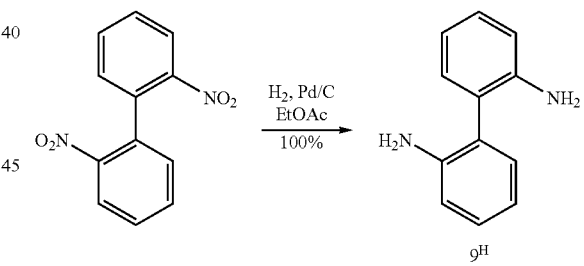

Synthesis of 2,2'-Diaminobiphenyl, Compound 9$^H$: Compound 9$^H$ was synthesized by an adaptation of a literature procedure, Gillespie et al. (2002) J. Org. Chem. 67:3450-3458. 2,2'-Dinitrobiphenyl (102.0 g, 417.5 mmol) and 10% Pd/C (16.4 g) were combined with 300 mL EtOAc in a hydrogenation vessel. The vessel was pressurized to 40 psi H$_2$ for 3.5 h (when H$_2$ was no longer being consumed). The slurry was filtered through a plug of celite. Rotary evaporation followed by drying on a vacuum line gave pure product as light yellow/orange powder in 100% yield. $^1$H NMR (CDCl$_3$, 297K, 300 MHz): δ 3.71 (s, 4H), δ 6.79 (dd, 2H, J=8.0, 1.2 Hz), δ 6.84 (td, 2H, J=7.4, 1.2 Hz), δ 7.12 (dd, 2H, J=8.0, 1.5 Hz), δ 7.19 (td, 2H, J=7.4, 1.5 Hz). $^{13}$C NMR (CDCl$_3$, 297K, 300 MHz): δ 115.58, δ 118.71, δ 124.62, δ 128.81, δ 131.08, δ 144.22. HRMS (ESI-EMM): m/z=185.1073 ([M+H]$^+$), Δ=2.7 ppm.

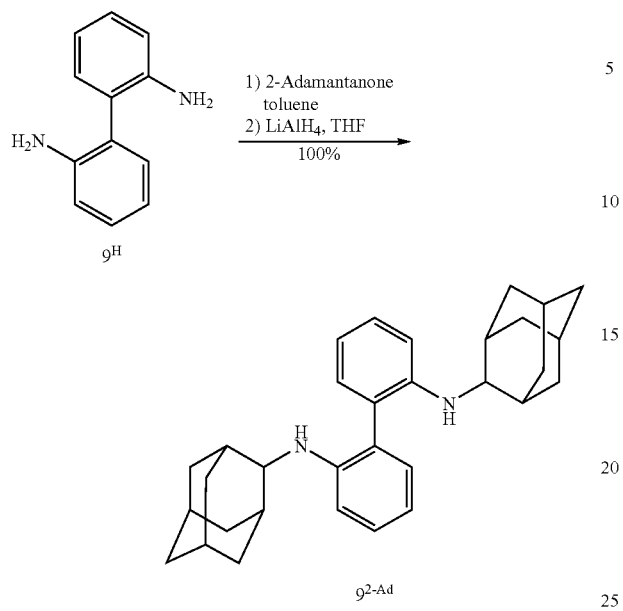

Synthesis of 2,2'-Bis(2-Adamantylamino)Biphenyl, Compound $9^{2-Ad}$. 614 mg (3.33 mmol) of 2,2'-diaminobiphenyl $9^H$ and 1 g (6.65 mmol) 2-adamantanone were combined with 1% (per amine functionality) pTsOH in a Dean-Stark apparatus. The reagents were dissolved in approximately 200 mL toluene and refluxed for 72 hours. The solvent was stripped off, and 122 mg (3.22 mmol) LAH was added, followed by approximately 200 mL THF. The reaction flask was heated to 50° C. for 2 h, followed by a careful quenching with approximately 100 mL water and 10 mL sat. NH$_4$Cl. The resulting slurry was filtered through a plug of celite, and the plug washed with CH$_2$Cl$_2$. The aqueous layer was washed once with CH$_2$Cl$_2$ (approx. 100 mL). The organic layers were combined, dried over MgSO$_4$, filtered, and the solvent was removed, yielding pure $9^{2-Ad}$ in 100% yield. $^1$H NMR (CDCl$_3$, 297K, 300 MHz): δ 1.38-1.97 (m, 28H), δ 3.54 (s, 2H), δ 4.05 (s, 2H), δ 6.71 (m, 4H), δ 7.11 (m, 2H), δ 7.22 (m, 2H). $^{13}$C NMR (CDCl$_3$, 297K, 300 MHz): δ 27.4, δ 27.6, δ 31.3, δ 31.7, δ 31.8, δ 32.2, δ 37.4, δ 37.8, δ 37.9, δ 56.7, δ 111.1, δ 116.3, δ 124.0, δ 129.1, δ 130.9, δ 145.3. HRMS (ESI-EMM): m/z=453.3247 ([M+H]$^+$), Δ=5 ppm.

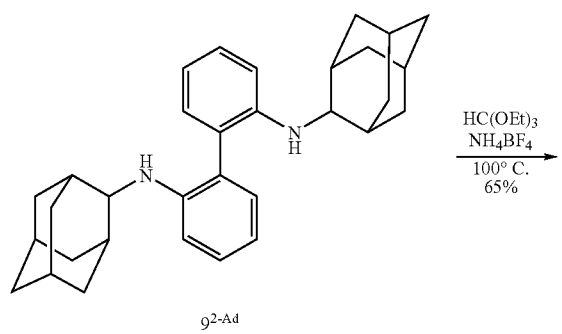

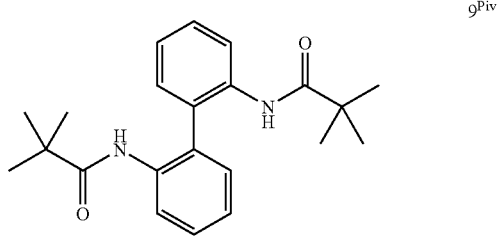

Synthesis of Amidinium Salt, Compound (±)10: Compound (±)10 was synthesized according to a modified literature procedure, see Alder et al. (2001) *J. Chem. Soc., Perkin Trans.* 1. 1586-1593, and Saba et al. (1991) *Tetrahedron Lett.* 32:5031-4. 5.76 g (12.7 mmol) of 2,2'-bis(2-adamantylamino)biphenyl $9^{2-Ad}$ and 1.3 g (12.7 mmol) NH$_4$BF$_4$ were combined under nitrogen in a 500 mL round-bottomed flask, and approx. 200 mL triethyl orthoformate was added. The reaction was heated to 100° C. for 16 h, after which time the product had crashed out of solution as a white powder. The reaction cooled to room temperature, was filtered, and the solid washed with diethyl ether followed by pentane to give the amidinium salt (±)10 in 65% yield as a light fluffy white powder without further purification. Crystals suitable for X-ray analysis were achieved by vapor diffusion of n-pentane onto a CHCl$_3$ solution of (±)10. $^1$H NMR (CDCl$_3$, 297K, 300 MHz): δ 0.97 (d, 2H, J=13.0 Hz), δ 1.14 (d, 2H, J=13.0 Hz), δ 1.47-2.09 (m, 22H), δ 2.66 (s, 2H), δ 4.77 (s, 2H), δ 7.43 (m, 2H), δ 7.51 (m, 6H), δ 8.84 (s, 1H). $^{13}$C NMR (CDCl$_3$, 297K, 300 MHz): δ 26.39, δ 26.74, δ 30.00, δ 30.11, δ 30.36, δ 31.71, δ 36.28, δ 36.38, δ 37.01, δ 65.55, δ 124.29, δ 129.48, δ 129.51, δ 129.56, δ 134.09, δ 143.97, δ 175.42. HRMS (ESI-EMM): m/z=453.3247 ([M−BF$_4$]+), Δ=3.0 ppm.

Synthesis of 2,2'-bis(pivaloylamino)-1,1'-biphenyl, Compound $9^{Piv}$. $9^H$ (6.50 g, 35.3 mmol) was weighed into an oven-dried 100 mL round-bottomed flask equipped with a stir bar and a septum-capped condenser, followed by N$_2$ purging. The system was charged with 70 mL dry THF and TEA (15.2 mL, 109 mmol). Pivaloyl chloride (11.3 mL, 91.7 mmol) was added dropwise via syringe to the above stirred solution, yielding a white precipitate. System was heated to reflux (80° C.) for 3 h under a N$_2$ atmosphere. The precipitate was filtered and washed with THF. Filtrate and washes were combined and liquids removed on a rotary evaporator giving pure $9^{Piv}$ as a white powder in 100% yield. $^1$H NMR (CDCl$_3$, 297K, 300 MHz): δ 1.00 (s, 18H), δ 7.18 (s, 2H), δ 7.24 (m, 4H), δ 7.46 (m, 2H), δ 8.32 (d, 2H, J=8.2 Hz). $^{13}$C NMR (CDCl$_3$, 297K, 250 MHz): δ 27.33, δ 39.80, δ 122.15, δ 124.79, δ 128.36, δ 129.76, δ 129.94, δ 136.25, δ 176.90.

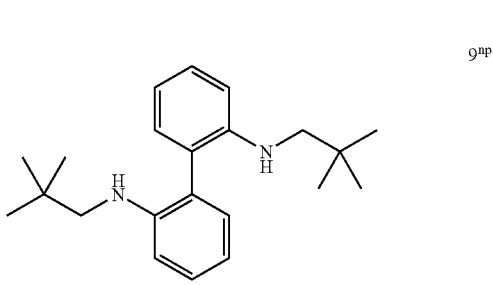

9$^{np}$

Synthesis of 2,2'-bis(neopentylamino)-1,1'-biphenyl, Compound 9$^{Np}$. An oven-dried 500 mL round-bottom flask equipped with a stir bar was charged with LAH (8.03 g, 211 mmol) in a dry box. The reaction vessel was capped with a septum, and 300 mL dry THF was added via syringe (outside of dry box). In a 100 mL oven-dried flask, 9$^{Piv}$ (12.44 g, 35.3 mmol) was dissolved in 200 mL dry THF under N$_2$, which was then slowly cannula transferred to the stirred LAH suspension. To the reaction vessel was attached an oven-dried septum-capped condenser with a N$_2$ inlet. The suspension was heated to reflux (80° C.) for 3.5 days, followed by careful quenching with H$_2$O until fizzing ceased to be visible. 2M NaOH$_{(aq)}$ was added until a clear THF layer could be seen. The slurry was filtered and the solid washed with THF. The layers were separated and the aqueous layer was washed twice with 200 mL THF. Organic layers were combined, dried over MgSO$_4$, and solvent removed to yield a mixture primarily consisting of starting material and product. The product was isolated as a clear oil in 91% yield by column chromatography (SiO$_2$, 7.5% EtOAc in hexanes). $^1$H NMR (CDCl$_3$, 297K, 300 MHz): δ 0.82 (s, 18H), δ 2.84 (m, 4H), δ 3.68 (t, 2H, J=5.1 Hz), δ 6.73 (m, 4H), δ 7.09 (m, 2H), δ 7.24 (m, 2H). $^{13}$C NMR (CDCl$_3$, 297K, 250 MHz): δ 27.8, δ 32.1, δ 55.8, δ 110.2, δ 116.6, δ 123.7, δ 129.2, δ 130.8, δ 146.8.

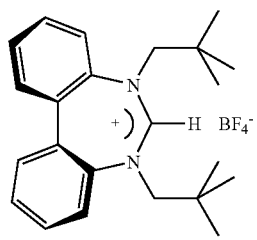

(±)11

Synthesis of neopentyl-substituted amidinium salt (±)-11. 9$^{Np}$ (10.3 g, 32.0 mmol) and NH$_4$BF$_4$ (3.36 g, 32.1 mmol) were combined in a 500 mL round-bottom flask equipped with a stir bar and topped with a condenser. 20 mL of triethyl orthoformate was added, and the system was heated to ca. 100° C. for 20 h. After cooling to room temperature, pentane was added (ca. 100 mL). The suspension was filtered, and the crystals washed with pentane to give (±)-11 as a white powdery solid in 93% yield. $^1$H NMR (CDCl$_3$, 297K, 300 MHz): δ 0.77 (s, 18H), δ 4.00 (s, 4H), δ 7.38 (m, 2H), δ 7.51 (m, 6H), δ 8.83 (s, 1H). $^{13}$C NMR (CDCl$_3$, 297K, 300 MHz): δ 27.1, δ 34.0, δ 66.4, δ 122.9, δ 130.0, δ 130.4, δ 130.6, δ 132.8, δ 146.3, δ 171.3. ESI-MS (m/z): calculated 335.2487, measured 335.2495.

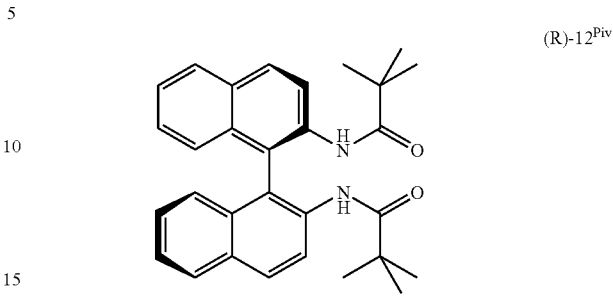

(R)-12$^{Piv}$

Synthesis of (R)-2,2'-bis(pivaloylamino)-1,1'-binaphthyl, Compound (R)-12$^{Piv}$. An oven-dried 100 mL flask fitted with a reflux condenser was charged with 500 mg (1.8 mmol) (R)-12$^H$ and 760 μL (5.45 mmol) TEA. 10 mL of dry THF was cannula transferred into the reaction vessel, followed by syringe addition of 560 μL (4.6 mmol) pivaloyl chloride. The reaction mixture was refluxed 2 h, then filtered. The volatiles were removed leaving pure (R)-12$^{Piv}$ in 100% yield as an off-white powder. $^1$H NMR (CDCl$_3$, 297K, 300 MHz): δ 0.75 (s, 18H), δ 7.14 (br. s., 2H), δ 7.18 (d, J=8.4 Hz, 2H), δ 7.32 (ddd, J=8.4, 6.9, 1.2 Hz, 2H), δ 7.46 (ddd, J=8.4, 6.9, 1.2 Hz, 2H), δ 7.95 (d, J=8.4 Hz, 2H), δ 8.05 (d, J=9.0 Hz, 2H), δ 8.48 (d, J=9.0 Hz, 2H).

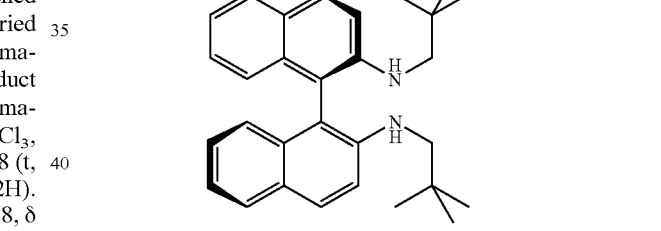

(R)-12$^{Np}$

Synthesis of (R)-2,2'-bis(neopentylamino)-1,1'-binaphthyl (R)-12$^{Np}$. See synthesis of 9$^{Np}$. 64% yield as an off-white powder. $^1$H NMR (CDCl$_3$, 297K, 300 MHz): δ 0.67 (s, 18H), δ 2.94 (AMX pattern, 4H), δ 3.73 (t, J=6.0 Hz, 2H), δ 7.00-7.03 (m, 2H), δ 7.11-7.17 (m, 4H), δ 7.25 (d, J=9.3 Hz, 2H), δ 7.75 (m, 2H), δ 7.85 (d, J=9.0 Hz).

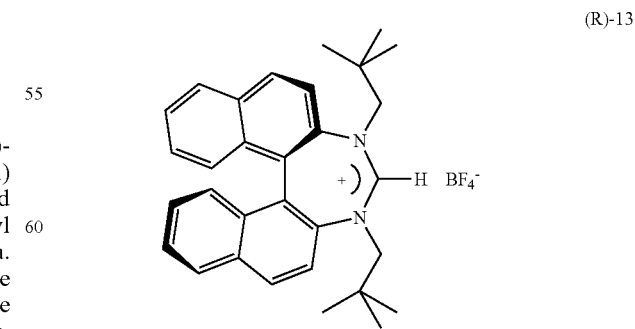

(R)-13

Amidinium Salt (R)-13. See synthesis of (±)-11. The product did not crash out of reaction, but was purified by removing excess orthoester under vacuum, dissolving in minimal CH$_2$Cl$_2$, and crashing out with pentane to give (R)-13 in 65% yield as a light fluffy off-white powder. $^1$H NMR (CDCl$_3$, 297K, 300 MHz): δ 0.64 (s, 18H), δ 4.01 (d, J=13.8 Hz, 2H), δ 4.20 (d, J=13.8 Hz, 2H), δ 7.07 (d, J=8.4 Hz, 2H), δ 7.34 (t, J=7.2 Hz, 2H), δ 7.62 (m, 4H), δ 8.00 (d, J=8.1 Hz, 2H), δ 8.12 (d, J=9.0 Hz), δ 8.85 (s, 1H). $^{13}$C NMR (CDCl$_3$, 297K, 300 MHz): δ 27.0, δ 33.9, δ 65.8, δ 120.2, δ 124.2, δ 126.4, δ 127.8, δ 128.1, δ 128.8, δ 131.5, δ 131.8, δ 132.9, δ 147.5, δ 173.1. ESI-MS (m/z): calculated 435.2800, measured 435.2794.

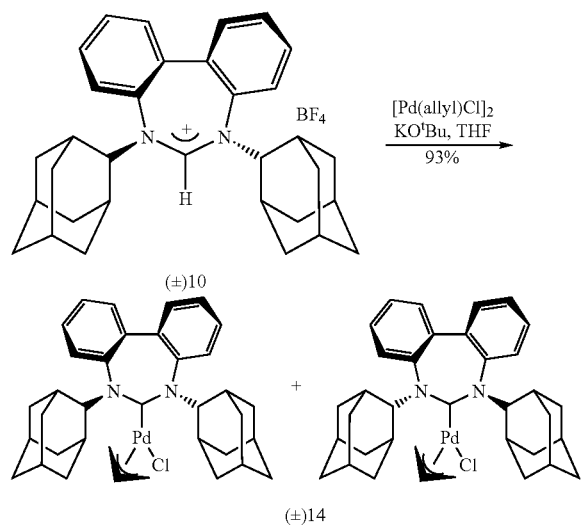

Synthesis of NHC—Pd(allyl)Cl, Compound (±)14. Compound (±)14 was synthesized according to an adaptation of a literature procedure. See Jensen & Sigman (2003) Org. Lett. 5:63-65. 200 mg (0.363 mmol) of aminidinium salt (±)10 and 78 mg (0.213 mmol) [Pd(allyl)Cl]$_2$ was combined with 1.2 eq of KO(t)Bu under nitrogen. The reaction was stirred in THF for 12 h, filtered through celite, and purified on a column under ambient conditions (SiO$_2$, 1:1 Ether:Hexanes) to give the NHC—Pd(Allyl)Cl complex (±)14 in 93% yield as a light yellow-tan solid. Crystals suitable for X-ray analysis were achieved by layering n-heptane onto a −20° C. ethereal solution of (±)14 followed by overnight diffusion at −20° C. Compound (±)14 crystallized as a 73:27 mixture of diastereomers. $^1$H NMR (CDCl$_3$, 297K, 500 MHz): δ 0.79-2.11 (m, 67.2H), δ 2.66 (s, 1.4H), δ 2.76 (d, 1.4H, J=11.0 Hz), δ 3.16-3.31 (m, 4.8H), δ 3.52 (s, 1H), δ 3.76 (d, 1H, J=6.0 Hz, 1H), δ 3.99-4.21 (m, 3.8H), δ 5.16 (m, 2.8H), δ 5.45 (m, 2H), δ 6.95 (m, 2.4H), δ 7.28-7.56 (m, 16.8H). $^{13}$C NMR (CDCl$_3$, 297K, 500 MHz): δ 26.5, δ 26.6, δ 26.7, δ 26.8, δ 26.9, δ 29.9, δ 30.0, δ 30.09, δ 30.11, δ 30.2, δ 30.4, δ 36.5, δ 31.1, δ 31.2, δ 36.1, δ 36.8, δ 37.0, δ 37.1, δ 37.2, δ 37.4, δ 37.5, δ 43.3, δ 46.1, δ 66.5, δ 66.6, δ 66.7, δ 66.9, δ 71.2, δ 73.1, δ 115.2, δ 124.7, δ 125.0, δ 126.7, δ 126.8, δ 126.9, δ 127.0, δ 127.1, δ 127.2, δ 127.6, δ 136.3, δ 136.4, δ 137.1, δ 146.2, δ 146.4, δ 146.6, δ 147.1. MS (ESI): m/z=(highest intensity peaks listed): 609.1 ([M−Cl]$^+$), 650.2 ([M+Li]$^+$), 667.2 ([M+Na]$^+$), 1255.3 ([M$_2$−Cl]$^+$).

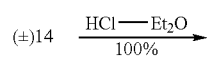

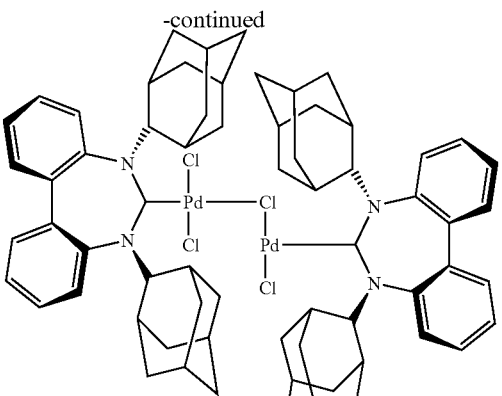

Synthesis of [NHC—Pd(Cl)$_2$]$_2$, Compound 15. Compound 15 was synthesized according to an adaptation of a literature procedure, see Jensen & Sigman (2003) Org. Lett. 5:63-65. A 50 mL round-bottomed flask was charged with 100 mg (0.16 mmol) (±)14 and 2.0 mL 2.0 M ethereal HCl. The color instantly changed to bright yellow-orange. 8.0 mL ether was added and the resultant suspension stirred for 1 h. Volatiles were removed in vacuo leaving pure 15 as a bright yellow-orange powder in quantitative yield. Compound 15 could be recrystallized by taking up in a small amount of toluene and crashing out with excess n-pentane (87%). Crystals suitable for X-ray analysis were achieved by vapor diffusion of n-pentane onto a CH$_2$Cl$_2$ solution of 15. $^1$H NMR (CDCl$_3$, 297K, 500 MHz): δ 0.67 (d, J=12.5 Hz, 2H), δ 0.94 (d, J=12.5 Hz, 2H), δ 1.26-2.37 (m, 20H), δ 4.5 (br. s, 1H), δ 4.8-5.7 (br. m, 3H), δ 7.27 (br. s, 2H), δ 7.34 (t, J=7.5 Hz, 4H), δ 7.45 (dd, J=7.5, 1.5 Hz, 2H). $^{13}$C NMR (CDCl$_3$, 297K, 500 MHz): δ 26.66, δ 26.98, δ 30.13, δ 30.49, δ 31.25, δ 35.81, δ 36.86, δ 37.24 (br.), δ 37.52, δ 68.10 (br.), δ 127.15, δ 127.28, δ 127.42, δ 127.79, δ 135.47, δ 145.78, δ 201.41. MS (ESI): m/z=(highest intensity peaks listed): 463.4 ([NHC+H]$^+$), 663.2 ([NHC—Pd(Cl)$_2$+Na]$^+$), 1303.6 ([M+Na]$^+$), 1380.7.

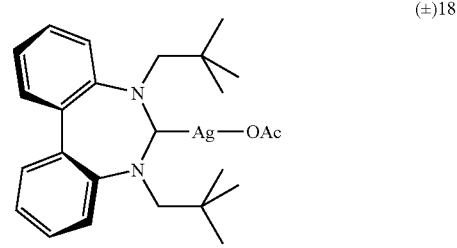

Synthesis of NHC—Ag—OAc complex (±)18. (±)11 (524 mg, 1.24 mmol), NaI (778 mg, 5.19 mmol), KO$^t$Bu (186 mg, 1.66 mmol), and Pd(OAc)$_2$ (278 mg, 1.24 mmol) were combined in a schlenk flask under a nitrogen atmosphere. After cooling to −78° C., 15 mL dry THF was added, and the solution was stirred overnight as the temperature slowly warmed to room temperature. Solvent was removed in a dry box, and residue was taken up in CH$_2$Cl$_2$. Filtration through a plug of celite gave a clear yellow/brown solution. Addition of AgOAc and stirring for 24 h gave a brown suspension with white ppt present. Filtration through celite, removal of solvent in vacuo, taking up in minimal $CH_2Cl_2$ and addition of excess hexanes gave a semi-cloudy light brown solution. Removal of small amount of solvent in vacuo promoted precipitation of an off-white solid, which was collected by filtration as pure (±)18 by NMR as a light tan powder in 18% yield. $^1$H NMR (CDCl$_3$, 297K, 300 MHz): δ 0.58 (s, 18H), δ 2.03 (s, 3H), δ 3.90 (d, 2H, J=13.4 Hz), δ 4.20 (d, 2H, J=13.4 Hz), δ 7.13 (m, 2H), δ 7.30 (m, 6H). $^{13}$C NMR (CDCl$_3$, 297K, 500 MHz): δ 27.8, δ 33.9, δ 71.9, δ 123.3, δ 127.8, δ 128.8, δ 129.0, δ 135.4, δ 149.5, δ 179.3 (s, carbene). MS (MALDI-TOF) (m/z): 335.3 ((NHC—H)$^+$), 441.0 (NHC—Ag$^+$), 774.9 ((NHC)$_2$Ag$^+$).

Crystallographic Experimental Data for Compound (±) 10: A colorless crystal with approximate dimensions 0.20×0.13×0.03 mm$^3$ was selected under oil under ambient conditions and attached to the tip of a nylon loop. The crystal was mounted in a stream of cold nitrogen at 100 K and centered in the X-ray beam by using a video camera.

The crystal evaluation and data collection were performed on a Bruker CCD-1000 diffractometer with Mo Kα (λ=0.71073 Å) radiation and the diffractometer to crystal distance of 4.9 cm.

The initial cell constants were obtained from three series of ω scans at different starting angles. Each series consisted of 30 frames collected at intervals of 0.3° in a 6° range about ω with the exposure time of 20 seconds per frame. A total of 59 reflections was obtained. The reflections were successfully indexed by an automated indexing routine built in the SMART program. The final cell constants were calculated from a set of 1,469 strong reflections from the actual data collection.

The data were collected by using the hemisphere data collection routine. The reciprocal space was surveyed to the extent of a full sphere to a resolution of 0.80 Å. A total of 12,112 data were harvested by collecting four sets of frames with 0.25° scans in ω with an exposure time 38 sec per frame. These highly redundant datasets were corrected for Lorentz and polarization effects. The absorption correction was based on fitting a function to the empirical transmission surface as sampled by multiple equivalent measurements. See Bruker-AXS (2000-2003) SADABS version 2.05, SAINT version 6.22, SHELXTL version 6.10 and SMART version 5.622 Software Reference Manuals, available from Bruker-AXS, Madison, Wis., USA.

Structure Solution and Refinement: The systematic absences in the diffraction data were consistent for the space groups C2/c and Cc. The E-statistics strongly suggested the centrosymmetric space group C2/c that yielded chemically reasonable and computationally stable results of refinement.

A successful solution by the direct methods provided all non-hydrogen atoms from the E-map. All non-hydrogen atoms were refined with anisotropic displacement coefficients. All hydrogen atoms were included in the structure factor calculation at idealized positions and were allowed to ride on the neighboring atoms with relative isotropic displacement coefficients.

The cation and the anion reside on different crystallographic two-fold rotation axes, which pass through atoms C(7) and B, respectively.

The final least-squares refinement of 182 parameters against 2,791 data resulted in residuals R (based on F2 for I≧2σ) and wR (based on F2 for all data) of 0.0495 and 0.1315, respectively. The final difference Fourier map was featureless. See FIG. 1 for the resulting molecular structure with thermal ellipsoids shown at 50% probability.

Crystallographic Experimental Data for Compound 14: A yellow crystal with approximate dimensions 0.46×0.25×0.15 mm$^3$ was selected under oil under ambient conditions and attached to the tip of a nylon loop. The crystal was mounted in a stream of cold nitrogen at 200(2) K and centered in the X-ray beam by using a video camera.

The crystal evaluation and data collection were performed on a Bruker CCD-1000 diffractometer with Mo Kα (λ=0.71073 Å) radiation and the diffractometer to crystal distance of 4.9 cm.

The initial cell constants were obtained from three series of ω scans at different starting angles. Each series consisted of 20 frames collected at intervals of 0.3° in a 6° range about ω with the exposure time of 10 seconds per frame. A total of 67 reflections was obtained. The reflections were successfully indexed by an automated indexing routine built in the SMART program. The final cell constants were calculated from a set of 5,499 strong reflections from the actual data collection.

The data were collected by using the hemisphere data collection routine. The reciprocal space was surveyed to the extent of a full sphere to a resolution of 0.80 Å. A total of 22,836 data were harvested by collecting three sets of frames with 0.3° scans in ω with an exposure time 30 sec per frame. These highly redundant datasets were corrected for Lorentz and polarization effects. The absorption correction was based on fitting a function to the empirical transmission surface as sampled by multiple equivalent measurements, as noted earlier.

Structure Solution and Refinement: The systematic absences in the diffraction data were uniquely consistent for the space group P2$_1$/c that yielded chemically reasonable and computationally stable results of refinement.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients unless otherwise indicated. All hydrogen atoms were included in the structure factor calculation at idealized positions and were allowed to ride on the neighboring atoms with relative isotropic displacement coefficients.

The allyl group is disordered over two positions in a 73:27 ratio and was refined with restraints. There is also one-half of solvated hexane molecule per Pd complex in the lattice. The solvent molecule was refined isotropically with restraints.

Figure 2:
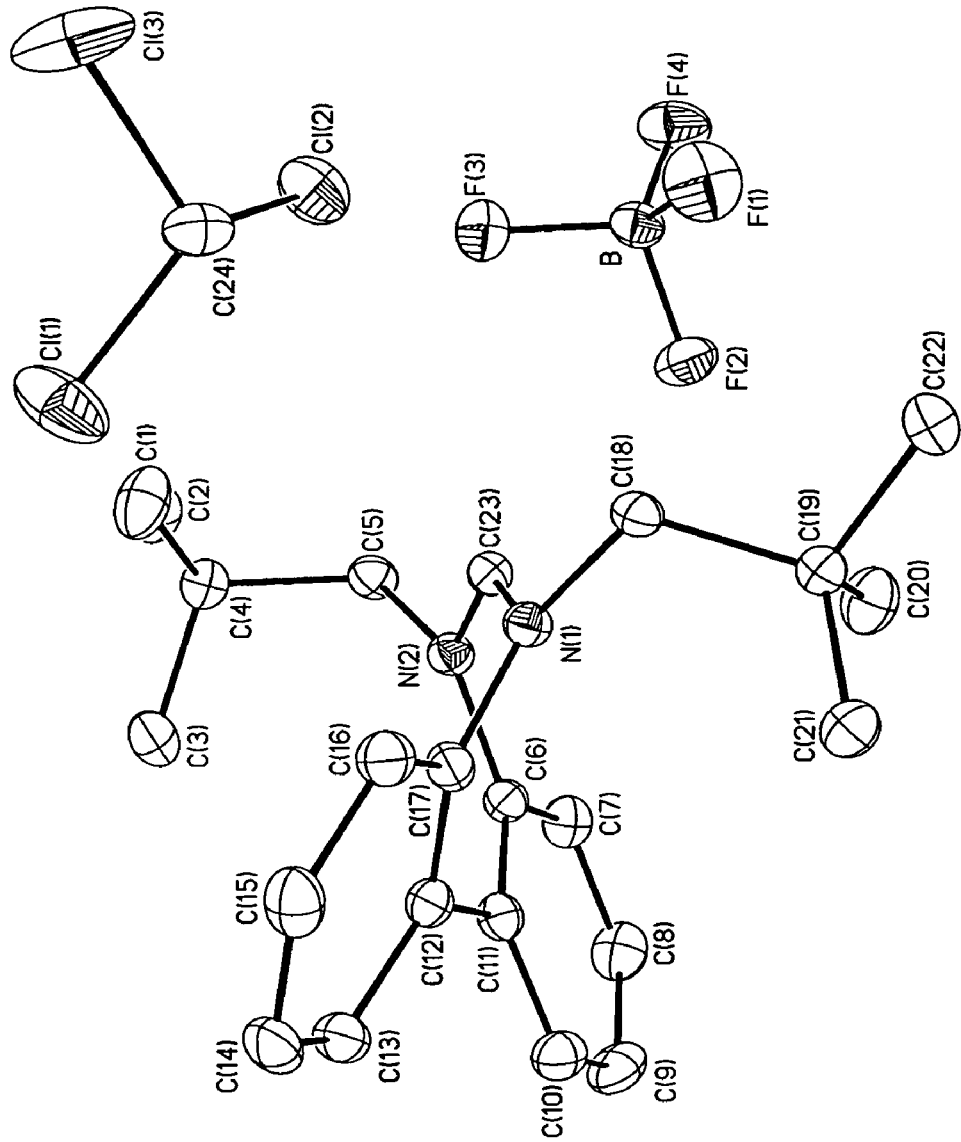
FIG. 2 is a depiction of the molecular structure of compound 11 as revealed by single-crystal X-ray diffraction. The hydrogen atoms are omitted for clarity. Thermal ellipsoids are shown at 50% probability.
Figure 3:
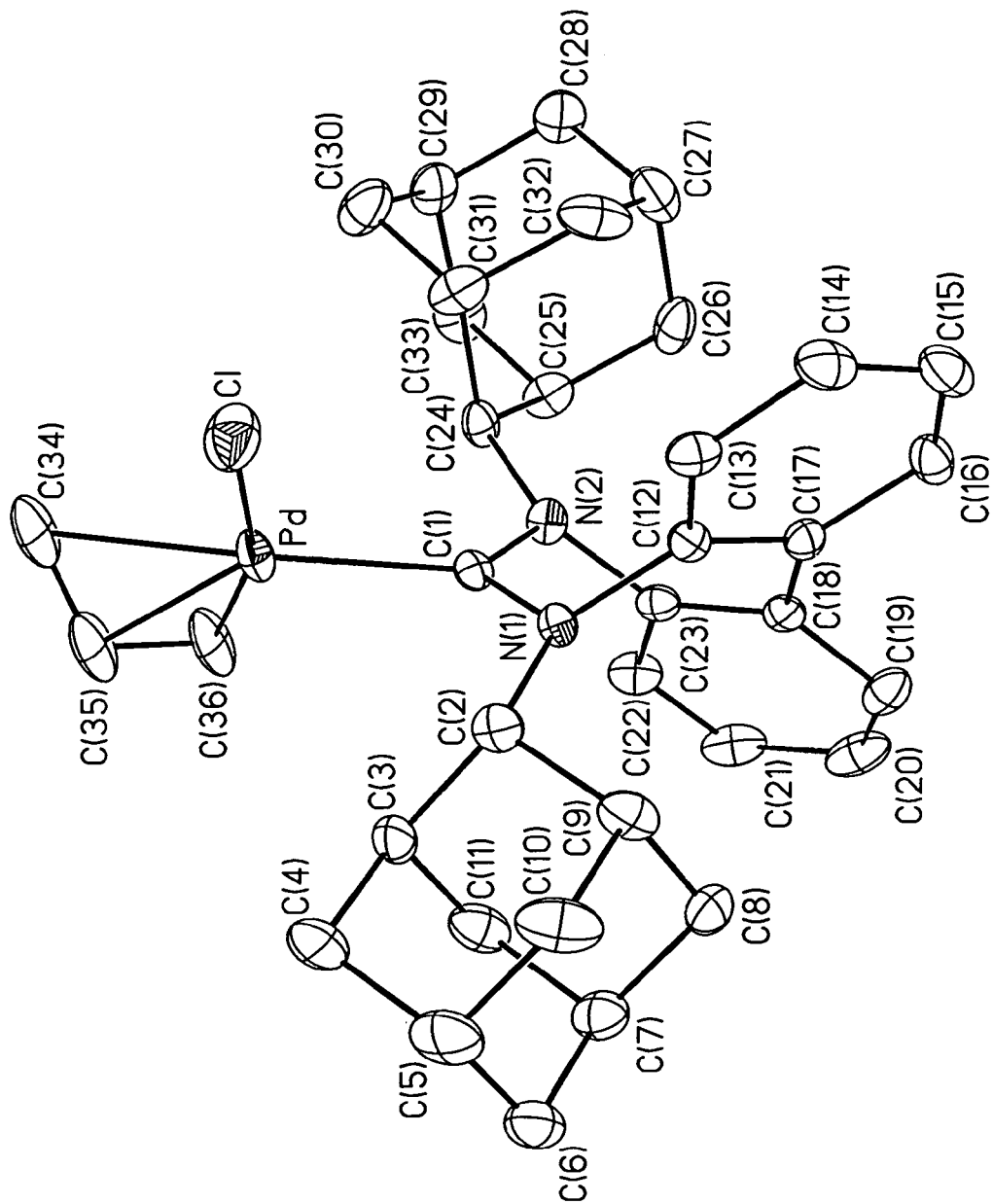
FIG. 3 is a depiction of the molecular structure of the palladium complex 14 as revealed by single-crystal X-ray diffraction. The hydrogen atoms and solvent molecules are omitted for clarity. Only the preferred orientation of the allyl group is shown.

The final least-squares refinement of 372 parameters against 5,613 data resulted in residuals R (based on F$^2$ for I≧2σ) and wR (based on F$^2$ for all data) of 0.0446 and 0.1194, respectively. The final difference Fourier map was featureless. The final molecular structures are shown in FIGS. 2 and 3. The molecular diagrams are drawn with 30% probability ellipsoids.

Crystallographic Experimental Data for Compound 15: A yellow crystal with approximate dimensions 0.40×0.35×0.17 mm$^3$ was selected under oil under ambient conditions and attached to the tip of a nylon loop. The crystal was mounted in a stream of cold nitrogen at 100 K and centered in the X-ray beam by using a video camera.

The crystal evaluation and data collection were performed on a Bruker CCD-1000 diffractometer with Mo Kα (λ=0.71073 Å) radiation and the diffractometer to crystal distance of 4.9 cm.

The initial cell constants were obtained from three series of ω scans at different starting angles. Each series consisted of 20 frames collected at intervals of 0.3° in a 6° range about ω with the exposure time of 10 seconds per frame. A total of 54 reflections was obtained. The reflections were successfully indexed by an automated indexing routine built in the SMART program. The final cell constants were calculated from a set of 11,665 strong reflections from the actual data collection.

The data were collected by using the hemisphere data collection routine. The reciprocal space was surveyed to the extent of a full sphere to a resolution of 0.80 Å. A total of 27,433 data were harvested by collecting three sets of frames with 0.30° scans in ω with an exposure time 30 sec per frame. These highly redundant datasets were corrected for Lorentz and polarization effects. The absorption correction was based on fitting a function to the empirical transmission surface as sampled by multiple equivalent measurements.

Structure Solution and Refinement: The systematic absences in the diffraction data were uniquely consistent for the space group $P2_1/n$ that yielded chemically reasonable and computationally stable results of refinement.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms were included in the structure factor calculation at idealized positions and were allowed to ride on the neighboring atoms with relative isotropic displacement coefficients. The Pd dimer occupies a crystallographic inversion center. There are four solvate molecules of $CH_2Cl_2$ per dimer in the lattice.

Figure 4:
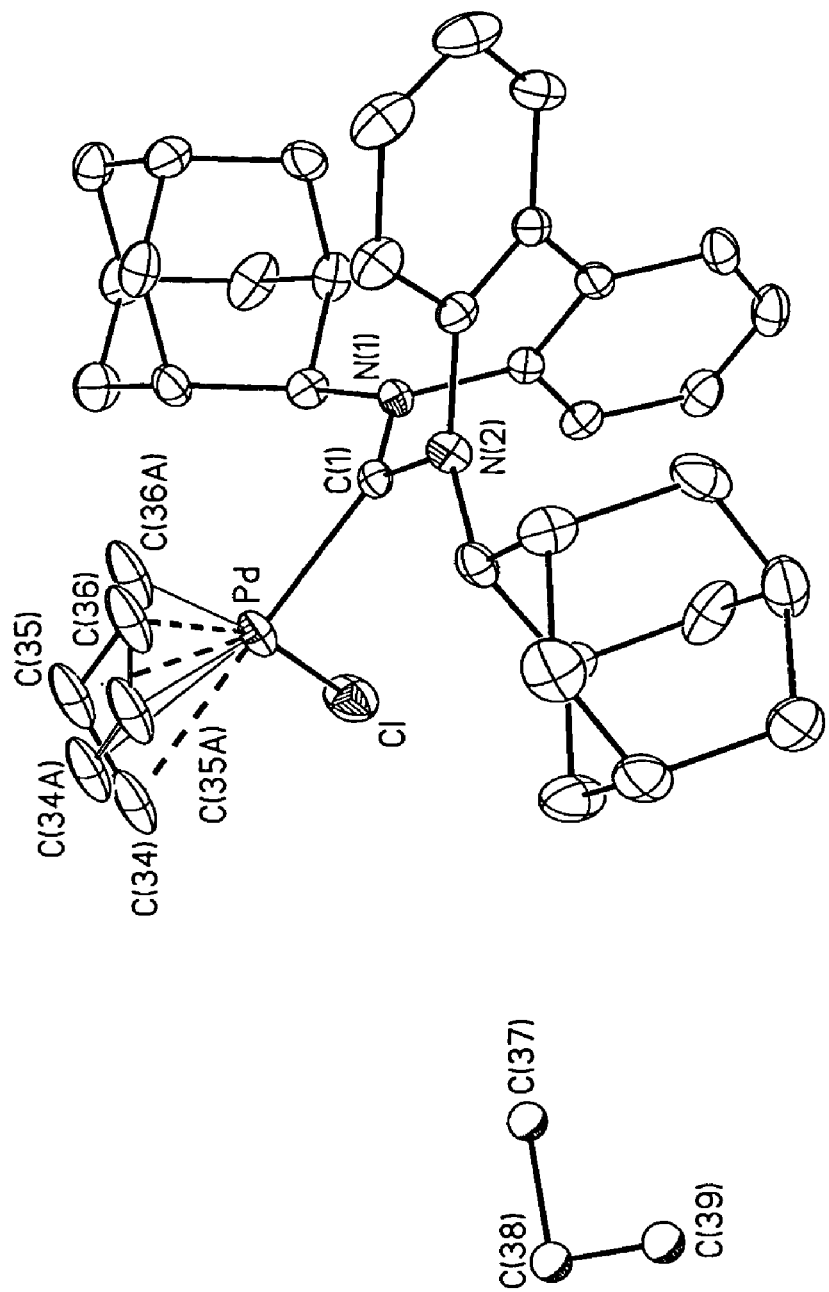
FIG. 4 is another depiction of the molecular structure of the palladium complex 14 as revealed by single-crystal X-ray diffraction. The hydrogen atoms are omitted for clarity. The allyl ligand is disordered in a 73:27 ratio.
Figure 5:
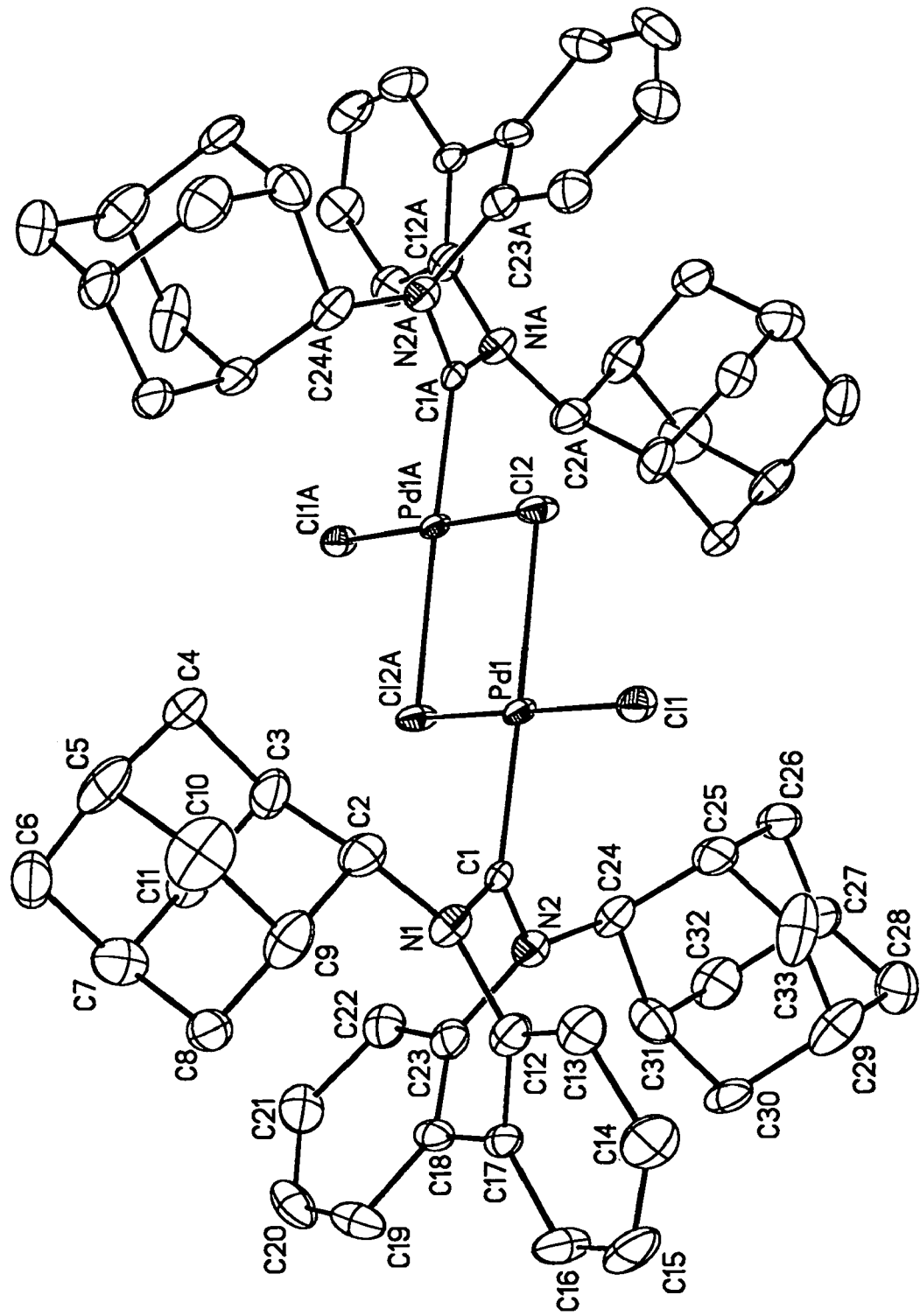
FIG. 5 is a depiction of the molecular structure of the palladium complex 15 as revealed by single-crystal X-ray diffraction. The hydrogen atoms and solvent molecules are omitted for clarity. Thermal ellipsoids are shown at 30% probability.

The final least-squares refinement of 397 parameters against 6,858 data resulted in residuals R (based on $F^2$ for $I \geq 2\sigma$) and wR (based on $F^2$ for all data) of 0.0689 and 0.1904, respectively. The resulting molecular structure is depicted in FIG. 4. The probability ellipsoids are at 30%. The content of the asymmetric unit of 12 is depicted in FIG. 5. The hydrogen atoms have been omitted in both FIGS. 4 and 5 for clarity.

Crystallographic Experimental Data for Compound 16: A yellow crystal with approximate dimensions 0.36×0.25×0.18 $mm^3$ was selected under oil under ambient conditions and attached to the tip of a nylon loop. The crystal was mounted in a stream of cold nitrogen at 100 K and centered in the X-ray beam by using a video camera.

The crystal evaluation and data collection were performed on a Bruker CCD-1000 diffractometer with Mo $K_\alpha$ ($\lambda$=0.71073 Å) radiation and the diffractometer to crystal distance of 4.9 cm.

The initial cell constants were obtained from three series of ω scans at different starting angles. Each series consisted of 20 frames collected at intervals of 0.3° in a 6° range about ω with the exposure time of 10 seconds per frame. A total of 76 reflections was obtained. The reflections were successfully indexed by an automated indexing routine built in the SMART program. The final cell constants were calculated from a set of 11009 strong reflections from the actual data collection.

The data were collected by using the full sphere data collection routine to survey the reciprocal space to the extent of a full sphere to a resolution of 0.80 Å. A total of 30455 data were harvested by collecting three sets of frames with 0.3° scans in ω with an exposure time 36 sec per frame. These highly redundant datasets were corrected for Lorentz and polarization effects. The absorption correction was based on fitting a function to the empirical transmission surface as sampled by multiple equivalent measurements.

Structure Solution and Refinement: The systematic absences in the diffraction data were consistent for the space groups Cc and C2/c. The E-statistics strongly suggested the centrosymmetric space group C2/c that yielded chemically reasonable and computationally stable results of refinement.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms were included in the structure factor calculation at idealized positions and were allowed to ride on the neighboring atoms with relative isotropic displacement coefficients.

There were two solvate molecules of dichloromethane and/or ether present in the asymmetric unit. A significant amount of time was invested in identifying and refining the disordered molecules. Bond length restraints were applied to model the molecules but the resulting isotropic displacement coefficients suggested the molecules were mobile. In addition, the refinement was computationally unstable. The "SQUEEZE" option in the computer program PLATON was used to correct the diffraction data for diffuse scattering effects and to identify the solvate molecule. (PLATON is a crystallographic modeling tool, copyright 1980-2005 by A. L. Spek, and can be obtained for free from Utrecht University, Padualaan 8, 3584 CH, Utrecht, The Netherlands.) PLATON calculated the upper limit of volume that can be occupied by the solvent to be 1558 $Å^3$, or 21% of the unit cell volume. The program calculated 689 electrons in the unit cell for the diffuse species. This approximately corresponds to two molecules of dichloromethane per Pd complex in the asymmetric unit (672 electrons). It is very likely that this solvate molecules are disordered over several positions. Note that all derived results in the following tables are based on the known contents. No data are given for the diffusely scattering species.

The final least-squares refinement of 414 parameters against 7613 data resulted in residuals R (based on $F^2$ for $I \geq 2\sigma$) and wR (based on $F^2$ for all data) of 0.0346 and 0.0960, respectively. The final difference Fourier map was featureless. The ORTEP diagram is drawn with 50% probability ellipsoids.

Crystallographic Experimental Data for Compound 16: A yellow crystal with approximate dimensions 0.47×0.26×0.23 $mm^3$ was selected under oil under ambient conditions and attached to the tip of a nylon loop. The crystal was mounted in a stream of cold nitrogen at 100 K and centered in the X-ray beam by using a video camera.

The crystal evaluation and data collection were performed on a Bruker CCD-1000 diffractometer with Mo $K_\alpha$ ($\lambda$=0.71073 Å) radiation and the diffractometer to crystal distance of 4.9 cm.

The initial cell constants were obtained from three series of ω scans at different starting angles. Each series consisted of 20 frames collected at intervals of 0.3° in a 6° range about ω with the exposure time of 10 seconds per frame. A total of 121 reflections was obtained. The reflections were successfully indexed by an automated indexing routine built in the SMART program. The final cell constants were calculated from a set of 9536 strong reflections from the actual data collection.

The data were collected by using the full sphere data collection routine to survey the reciprocal space to the extent of a full sphere to a resolution of 0.80 Å. A total of 27822 data were harvested by collecting three sets of frames with 0.3° scans in ω with an exposure time 36 sec per frame. These highly redundant datasets were corrected for Lorentz and polarization effects. The absorption correction was based on fitting a function to the empirical transmission surface as sampled by multiple equivalent measurements.

Structure Solution and Refinement: The systematic absences in the diffraction data were uniquely consistent for the space group $P2_1/n$ that yielded chemically reasonable and computationally stable results of refinement.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients unless specified otherwise. All hydrogen atoms were included in the structure factor calculation at idealized positions and were allowed to ride on the neighboring atoms with relative isotropic displacement coefficients.

The carbene ligand is disordered over two positions in a 63:37 ratio and was refined with an idealized geometry. All atoms of the carbene ligand were refined isotropically. The ligand disorder resulted in multiple positions of the adamantyl groups. Two positions for each group were identified and refined. The residual peaks of electron density suggested that a third orientation for each adamantyl group could be present. After considerable effort was spent on identifying and refining the third locations it was decided that these orientations of the adamantyl group did not clearly correspond to chemically reasonable positions and their incorporation into the model resulted in only slight overall improvement of the structural refinement. Thus, the possible third positions were ignored and only two positions for each adamantyl substituent are presented in the current report.

The final least-squares refinement of 344 parameters against 6950 data resulted in residuals R (based on $F^2$ for $I \geq 2\sigma$) and wR (based on $F^2$ for all data) of 0.1034 and 0.2651, respectively.

Crystallographic Experimental Data for Compound 18: A colorless crystal with approximate dimensions 0.29×0.23×0.19 mm$^3$ was selected under oil under ambient conditions and attached to the tip of a nylon loop. The crystal was mounted in a stream of cold nitrogen at 200(2) K and centered in the X-ray beam by using a video camera.

The crystal evaluation and data collection were performed on a Bruker CCD-1000 diffractometer with Mo $K_\alpha$ ($\lambda$=0.71073 Å) radiation and the diffractometer to crystal distance of 4.9 cm.

The initial cell constants were obtained from three series of $\omega$ scans at different starting angles. Each series consisted of 20 frames collected at intervals of 0.3° in a 6° range about $\omega$ with the exposure time of 15 seconds per frame. A total of 206 reflections was obtained. The reflections were successfully indexed by an automated indexing routine built in the SMART program. The final cell constants were calculated from a set of 10935 strong reflections from the actual data collection.

The data were collected by using the hemisphere data collection routine. The reciprocal space was surveyed to the extent of a full sphere to a resolution of 0.80 Å. A total of 24283 data were harvested by collecting three sets of frames with 0.25° scans in $\omega$ with an exposure time 25 sec per frame. These highly redundant datasets were corrected for Lorentz and polarization effects. The absorption correction was based on fitting a function to the empirical transmission surface as sampled by multiple equivalent measurements.

Structure Solution and Refinement: The systematic absences in the diffraction data were uniquely consistent for the space group $P2_1/n$ that yielded chemically reasonable and computationally stable results of refinement.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms were included in the structure factor calculation at idealized positions and were allowed to ride on the neighboring atoms with relative isotropic displacement coefficients.

The toluene solvent molecule is equally disordered over two positions and was refined with soft restraints and constraints.

The final least-squares refinement of 383 parameters against 6155 data resulted in residuals R (based on $F^2$ for $I \geq 2\sigma$) and wR (based on $F^2$ for all data) of 0.0273 and 0.0719, respectively. The final difference Fourier map was featureless.

What is claimed is:
1. A N-heterocyclic carbene of formula I:

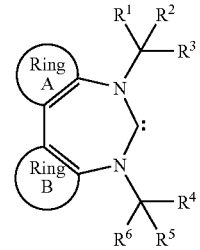

or a salt or metal complex thereof;
wherein ring A and ring B are independently selected from the group consisting of substituted or unsubstituted phenyl, naphthalenyl, and 9,10-dihydrophenanthrenyl;
wherein when ring A or ring B is substituted, substituents are selected from the group consisting of halogen; linear or branched $C_1$-$C_{12}$-alkyl, alkenyl, or alkynyl; $C_5$-$C_{12}$-cycloalkyl, cycloalkenyl, or cycloalkynyl; mono- or polycyclic aryl, and mono- or polycyclic heteroaryl having up to 5 heteroatoms selected from N, O, S, and P;
wherein $R^1$, $R^2$, $R^3$ and the carbon to which they are attached, and $R^4$, $R^5$, $R^6$, and the carbon to which they are attached, are adamantyl; and
salts thereof; and
metal complexes thereof.

2. An amidinium salt of N-heterocyclic carbene of formula I:

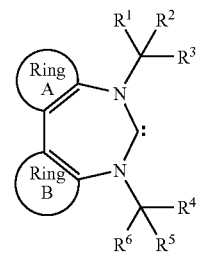

wherein ring A and ring B are independently selected from the group consisting of substituted or unsubstituted phenyl, naphthalenyl, and 9,10-dihydrophenanthrenyl;

$R^1$, $R^2$, $R^3$, $R^4$, $R^5$, and $R^6$ are independently selected from the group consisting of hydrogen; $C_1$ to $C_{60}$ substituted or unsubstituted, linear or branched alkyl, alkenyl, and alkynyl, aryl and heteroaryl; or $R^1$, $R^2$, and $R^3$, including or excluding the carbon to which they are attached and independent of $R^4$, $R^5$, and $R^6$, and $R^4$, $R^5$, and $R^6$, including or excluding the carbon to which they are attached and independent of $R^1$, $R^2$, and $R^3$, define a $C_3$ to $C_{60}$, substituted or unsubstituted, mono- or polycyclic cycloalkyl, cycloalkenyl, cycloalkynyl, cycloaryl, heterocycloaryl, heterocycloalkenyl, heterocycloaklynyl, wherein heteroatoms in if any, are independently selected from the group consisting of N, O, S, and P;

wherein substituents on substituted moieties are selected from the group consisting of halogen; linear or branched $C_1$-$C_{12}$-alkyl, alkenyl, or alkynyl; $C_5$-$C_{12}$-cycloalkyl, cycloalkenyl, or cycloalkynyl; mono- or polycyclic aryl, and mono- or polycyclic heteroaryl having up to 5 heteroatoms selected from N, O, S, and P.

3. A N-heterocyclic carbene of formula II:

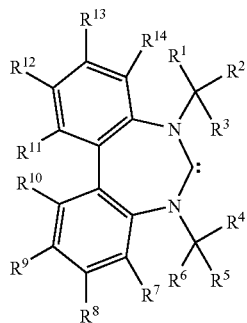

or a salt or metal complex thereof;

wherein $R^1$, $R^2$, $R^3$, $R^4$, $R^5$, and $R^6$ are independently selected from the group consisting of hydrogen; $C_1$ to $C_{60}$ substituted or unsubstituted, linear or branched alkyl, alkenyl, and alkynyl, aryl and heteroaryl; or $R^1$, $R^2$, and $R^3$, including or excluding the carbon to which they are attached and independent of $R^4$, $R^5$, and $R^6$, and $R^4$, $R^5$, and $R^6$, including or excluding the carbon to which they are attached and independent of $R^1$, $R^2$, and $R^3$, define a $C_3$ to $C_{60}$, substituted or unsubstituted, mono- or polycyclic cycloalkyl, cycloalkenyl, cycloalkynyl, cycloaryl, heterocycloaryl, heterocycloalkenyl, heterocycloaklynyl, wherein heteroatoms in if any, are independently selected from the group consisting of N, O, S, and P;

wherein substituents on substituted moieties are selected from the group consisting of halogen; linear or branched $C_1$-$C_{12}$-alkyl, alkenyl, or alkynyl; $C_5$-$C_{12}$-cycloalkyl, cycloalkenyl, or cycloalkynyl; mono- or polycyclic aryl, and mono- or polycyclic heteroaryl having up to 5 heteroatoms selected from N, O, S, and P;

and wherein any of $R^7$, $R^8$, $R^9$, and $R^{10}$ combined any of $R^{11}$, $R^{12}$, $R^{13}$, and $R^{14}$ combined independently define substituted or unsubstituted phenyl;

salts thereof; and metal complexes thereof.

4. A N-heterocyclic carbene of formula II:

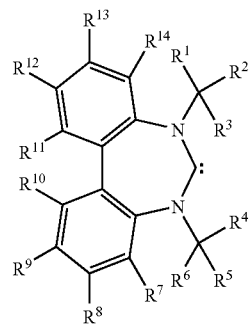

or a salt or metal complex thereof;

wherein $R^1$, $R^2$, $R^3$ and the carbon to which they are attached, and $R^4$, $R^5$, $R^6$, and the carbon to which they are attached, are adamantyl; and $R^7$, $R^8$, $R^9$, $R^{10}$, $R^{11}$, $R^{12}$, $R^{13}$, and $R^{14}$ are independently selected from the group consisting of hydrogen, halo, $C_1$ to $C_{60}$ substituted or unsubstituted, linear or branched alkyl, alkenyl, and alkynyl, aryl, heteroaryl, cyano, thiolate, alkoxy, primary amido, and secondary amido; or any of $R^7$, $R^8$, $R^9$, and $R^{10}$ combined and any of $R^{11}$, $R^{12}$, $R^{13}$, and $R^{14}$ combined independently define substituted or unsubstituted phenyl;

wherein substituents on substituted moieties are selected from the group consisting of halogen; linear or branched $C_1$-$C_{12}$-alkyl, alkenyl, or alkynyl; $C_5$-$C_{12}$-cycloalkyl, cycloalkenyl, or cycloalkynyl; mono- or polycyclic aryl, and mono- or polycyclic heteroaryl having up to 5 heteroatoms selected from N, O, S, and P; and salts thereof; and metal complexes thereof.

5. An amidinium salt of N-heterocyclic carbene of formula II:

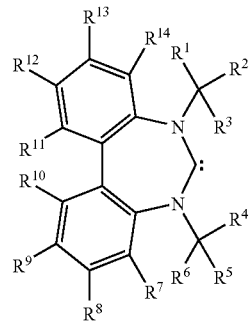

wherein $R^1$, $R^2$, $R^3$, $R^4$, $R^5$, and $R^6$ are independently selected from the group consisting of hydrogen; $C_1$ to $C_{60}$ substituted or unsubstituted, linear or branched alkyl, alkenyl, and alkynyl, aryl and heteroaryl; or $R^1$, $R^2$, and $R^3$, including or excluding the carbon to which they are attached and independent of $R^4$, $R^5$, and $R^6$, and $R^4$, $R^5$, and $R^6$, including or excluding the carbon to which they are attached and independent of $R^1$, $R^2$, and $R^3$, define a $C_3$ to $C_{60}$, substituted or unsubstituted, mono- or polycyclic cycloalkyl, cycloalkenyl, cycloalkynyl, cycloaryl, heterocycloaryl, heterocycloalkenyl, heterocycloaklynyl, wherein heteroatoms in if any, are independently selected from the group consisting of N, O, S, and P;
wherein substituents on substituted moieties are selected from the group consisting of halogen; linear or branched $C_1$-$C_{12}$-alkyl, alkenyl, or alkynyl; $C_5$-$C_{12}$-cycloalkyl, cycloalkenyl, or cycloalkynyl; mono- or polycyclic aryl, and mono- or polycyclic heteroaryl having up to 5 heteroatoms selected from N, O, S, and P; and wherein any of $R^7$, $R^8$, $R^9$, and $R^{10}$ combined and any of $R^{11}$, $R^{12}$, $R^{13}$, and $R^{14}$ combined independently define substituted or unsubstituted phenyl.

* * * * *